US012649936B2

(12) United States Patent (10) Patent No.: US 12,649,936 B2
Zhou et al. (45) Date of Patent: Jun. 9, 2026

(54) P450 CYTOCHROME ENZYME FOR ANDROGRAPHOLIDE SYNTHESIS AND ITS APPLICATION

(71) Applicant: Jiangnan University, Wuxi (CN)

(72) Inventors: Jingwen Zhou, Wuxi (CN); Shan Li, Wuxi (CN); Song Gao, Wuxi (CN); Sha Xu, Wuxi (CN); Weizhu Zeng, Wuxi (CN); Shiqin Yu, Wuxi (CN)

(73) Assignee: Jiangnan University, Wuxi (CN)

( * ) Notice: Subject to any disclaimer, the term of this patent is extended or adjusted under 35 U.S.C. 154(b) by 334 days.

(21) Appl. No.: 18/541,098

(22) Filed: Dec. 15, 2023

(65) Prior Publication Data

US 2024/0117387 A1     Apr. 11, 2024

(30) Foreign Application Priority Data

Dec. 24, 2022    (CN) .......................... 202211669385.1

(51) Int. Cl.
| | |
|---|---|
| *C12P 7/02* | (2006.01) |
| *C12N 9/10* | (2006.01) |
| *C12N 9/88* | (2006.01) |
| *C12N 15/81* | (2006.01) |
| *C12P 5/00* | (2006.01) |

(52) U.S. Cl.
CPC .............. *C12P 7/02* (2013.01); *C12N 9/1085* (2013.01); *C12N 9/88* (2013.01); *C12N 15/81* (2013.01); *C12P 5/002* (2013.01); *C12Y*

*205/01* (2013.01); *C12Y 402/03028* (2013.01); *C12N 2800/102* (2013.01)

(58) Field of Classification Search
CPC ................ C12P 5/002; C12P 7/02; C12P 7/42
See application file for complete search history.

(56) References Cited

U.S. PATENT DOCUMENTS

2024/0117387 A1* 4/2024 Zhou ....................... C12P 5/002

* cited by examiner

*Primary Examiner* — Tekchand Saidha
(74) *Attorney, Agent, or Firm* — IPro, PLLC; Na Xu

(57) ABSTRACT

The present disclosure provides a P450 cytochrome enzyme for andrographolide synthesis and its application, belonging to the field of bioengineering. The present disclosure uses *Saccharomyces cerevisiae* CEN.PK2-1D as a host, and implements knockout of ROX1 and GAL80 genes on the genome, and integrative expression of GGPP synthase encoding gene and CPS diterpene synthase encoding gene at ROX1 site; and implements free expression of ApCPR and CYP71A8 and CYP71D10 both with truncated signal peptides, successfully constructing recombinant *S. cerevisiae*, and achieving de novo synthesis of 3,15,19-Trihydroxy-8 (17),13-ent-labdadiene-16-oic acid. Compared with the blank, a response value of a product peak reaches 1.9*106, and this strategy provides necessary reference for analyzing biosynthetic pathway of andrographolide and using metabolic engineering to synthesize andrographolide and related derivatives thereof.

6 Claims, 3 Drawing Sheets

Specification includes a Sequence Listing.

P450 CYTOCHROME ENZYME FOR ANDROGRAPHOLIDE SYNTHESIS AND ITS APPLICATION

REFERENCE TO SEQUENCE LISTING

The instant application contains a Sequence Listing in XML format as a file named "YGHY-2023-50-SEQ.xml", created on Dec. 13, 2023, of 69.7 kB in size, and which is hereby incorporated by reference in its entirety.

TECHNICAL FIELD

The present disclosure relates to a P450 cytochrome enzyme for andrographolide synthesis and its application, belonging to the field of applied microbiology and enzyme engineering.

BACKGROUND

Cytochrome P450 (P450) belongs to the heme oxygenase superfamily, named after the maximum absorption peak near 450 nm when the reduced heme oxygenase forms a complex with CO. According to the cellular localization of P450 enzymes and the composition of redox partner proteins (NADPH-cytochrome P450 reductase, CPR), they can be divided into 5 classes. Class I requires additional electron transport proteins to transfer electrons NAD(P)H to P450 enzymes active center to complete the entire catalytic process.

ent-Copalol and 3,15,19-Trihydroxy-8(17),13-ent-labdadiene-16-oic acid are diterpene compounds containing four isoprenes, which are present in herb *Andrographis paniculata* and are important intermediate compounds for synthesis of andrographolide. Andrographolide has heat-clearing, detoxifying, swelling reducing and analgesic effects, and is known as a "natural antibiotic drug". However, there are currently no reports on catalytic reactions of the P450 enzymes and pathway substances 3,15,19-Trihydroxy-8(17),13-ent-labdadiene-16-oic acid for the synthesis of andrographolide. Therefore, studying the activity and function of CYP450 enzymes in the synthesis process is of great significance for understanding the entire synthesis pathway of andrographolide.

CYP450 enzymes are membrane proteins, and their formation requires a series of post-translational modifications. Eukaryotic expression hosts have a relatively complete post-translational modification system including endoplasmic reticulum, Golgi apparatus and other inner membrane structures, making the expressed heterologous protein closer to their natural conformation. Eukaryotic microorganisms are usually considered suitable systems for heterologous expression of CYP450 enzymes. In addition, endogenous CPR of eukaryotic microorganisms can mediate effective transfer of electrons to the CYP450 enzymes, helping the CYP450 enzymes to exert their catalytic function. The natural advantages of eukaryotic microorganisms are applied in catalytic synthesis of 3,15,19-Trihydroxy-8(17), 13-ent-labdadiene-16-oic acid (FIG. 1). According to the existing research, there is currently no eukaryotic microbial recombinant strains for de novo synthesis of 3,15,19-Trihydroxy-8(17),13-ent-labdadiene-16-oic acid.

SUMMARY

In the present disclosure, CYP71A8 and CYP71D10 derived from *Andrographis paniculata* belong to the Class I CYP71 family and require electron transport protein to catalyze their activity, but their specific biological functions have not been reported. Therefore, the present disclosure is the first to perform heterologous expression of CYP71A8 and CYP71D10 and provide their catalytic functions.

A first objective of the present disclosure is to provide application of CYP450 enzymes derived from *Andrographis paniculata* in catalytic synthesis of 3,15,19-Trihydroxy-8 (17),13-ent-labdadiene-16-oic acid.

In one embodiment, the CYP450 enzymes derived from *Andrographis paniculata* are CYP71A8 and CYP71D10.

In one embodiment, a nucleotide sequence of the CYP71A8 is shown in SEQ ID NO:1; and a nucleotide sequence of the CYP71D10 is shown in SEQ ID NO:2.

In one embodiment, the CYP71A8 has N-terminal truncated by 32 amino acids, and the CYP71D10 has N-terminal truncated by 28 amino acids.

In one embodiment, a nucleotide sequence of the CYP71A8 with N-terminal truncated by 32 amino acids is shown in SEQ ID NO:3, and a nucleotide sequence of the CYP71D10 with N-terminal truncated by 28 amino acids is shown in SEQ ID NO:4.

A second objective of the present disclosure is to provide a recombinant *Saccharomyces cerevisiae*, including knockout of ROX1 and GAL80 genes on the genome; integrative expression of a GGPP synthase encoding gene and CPS diterpene synthase encoding gene; and free expression of CYP71A8 encoding gene CYP71A8t with N-terminal truncated by 32 amino acids, CYP71A10 encoding gene CYP71D10t with N-terminal truncated by 28 amino acids, and CPR encoding gene ApCPR.

In one embodiment, after the knockout of ROX1 site, the GGPP synthase encoding gene and the CPS diterpene synthase encoding gene are integrated at the ROX1 site.

In one embodiment, a nucleotide sequence of the CYP71A8 with N-terminal truncated by 32 amino acids is shown in SEQ ID NO:3, and a nucleotide sequence of the CYP71D10 with N-terminal truncated by 28 amino acids is shown in SEQ ID NO:4.

In one embodiment, a nucleotide sequence of the ApCPR is shown in SEQ ID NO:7.

In one embodiment, a nucleotide sequence of the GGPP synthase is shown in SEQ ID NO:8.

In one embodiment, a nucleotide sequence of the CPS diterpene synthase is shown in SEQ ID NO:9.

In one embodiment, *S. cerevisiae* CEN.PK2-1D is used as a starting strain.

In one embodiment, promoter $P_{PGK1}$ is used for starting expression of the CPR encoding gene.

In one embodiment, promoter $P_{TEF1}$ is used for starting expression of the CYP71A8t.

In one embodiment, promoter $P_{GAL7}$ is used for starting expression of the CYP71D10t.

In one embodiment, a nucleotide sequence of the promoter $P_{GAL7}$ is shown in SEQ ID NO:10, a nucleotide sequence of the promoter $P_{PGK1}$ is shown in SEQ ID NO:11, and a nucleotide sequence of the promoter $P_{TEF1}$ is shown in SEQ ID NO:12.

In one embodiment, pY26 series vectors or pET series vectors are used as expression vectors.

In one embodiment, the pET series vectors include a pET22b(+) expression vector or a pET28a(+) expression vector.

A third objective of the present disclosure is to provide a whole-cell catalyst, which contains the above-mentioned recombinant *S. cerevisiae*.

A fourth objective of the present disclosure is to provide a method for synthesizing 3,15,19-Trihydroxy-8(17),13-ent-labdadiene-16-oic acid, using the above-mentioned recombinant *S. cerevisiae* or the above-mentioned whole-cell catalyst as a fermentation strain for fermentation to produce 3,15,19-Trihydroxy-8(17),13-ent-labdadiene-16-oic acid.

In one embodiment, the method includes fermentation to produce in a culture medium using glucose as a carbon source.

In one embodiment, the method includes inoculating seed liquid of the above-mentioned recombinant *S. cerevisiae* or the above-mentioned whole-cell catalyst into the culture medium, and fermenting at 28-32° C. and 200-230 rpm for 90-160 h.

In one embodiment, the culture medium includes 10-30 g/L peptone, 5-15 g/L yeast powder, and 10-30 g/L glucose.

In one embodiment, a method for preparing the seed liquid includes inoculating the above-mentioned recombinant *S. cerevisiae* or the above-mentioned whole-cell catalyst into a seed culture medium, and fermenting at 28-32° C. and 200-230 rpm for 12-20 h.

The present disclosure further provides application of the CYP450 enzymes derived from *Andrographis paniculata*, or the above-mentioned recombinant *S. cerevisiae*, or the above-mentioned whole-cell catalyst, or the above-mentioned method in catalytic synthesis of andrographolide or products containing andrographolide.

In one embodiment, the CYP450 enzymes derived from *Andrographis paniculata* are CYP71A8 and CYP71D10.

In one embodiment, a nucleotide sequence of the CYP71A8 is shown in SEQ ID NO:1; and a nucleotide sequence of the CYP71D10 is shown in SEQ ID NO:2.

In one embodiment, the CYP71A8 has N-terminal truncated by 32 amino acids, and the CYP71D10 has N-terminal truncated by 28 amino acids.

In one embodiment, a nucleotide sequence of the CYP71A8 with N-terminal truncated by 32 amino acids is shown in SEQ ID NO:3, and a nucleotide sequence of the CYP71D10 with N-terminal truncated by 28 amino acids is shown in SEQ ID NO:4.

The present disclosure further provides application of the above-mentioned recombinant *S. cerevisiae*, or the above-mentioned whole-cell catalyst, or the above-mentioned method in catalytic synthesis of 3,15,19-Trihydroxy-8(17), 13-ent-labdadiene-16-oic acid or products containing 3,15, 19-Trihydroxy-8(17),13-ent-labdadiene-16-oic acid.

The Present Disclosure has the Following Beneficial Effects:

1. The present disclosure uses BL21 (DE3) as a host to express recombinant plasmids pET22b(+)-CYP71A8t and pET28a(+)-CYP71D10t, uses obtained recombinant *Escherichia coli* to successfully implement heterologous expression of CYP7A8 and CYP71D10 with truncated signal peptides, and finds that the protein loses expression activity when CYP71A8 is truncated to 57 amino acids, and the protein loses expression activity when CYP71D10 is truncated to 59 amino acids.

2. The present disclosure uses *S. cerevisiae* CEN.PK2-1D as a host, and implements knockout of the ROX1 and GAL80 genes on the genome, and integrative expression of the GGPP synthase encoding gene and the CPS diterpene synthase encoding gene at the ROX1 site; and implements free expression of CYP71A8 and CYP71D10 and ApCPR, successfully constructing recombinant *S. cerevisiae* CW1006/pY26-P$_{TEF1}$-CYP71A8t-P$_{GAL7}$-CYP71D10t, and achieving microbial fermentation to synthesize 3,15,19-Trihydroxy-8(17),13-ent-labdadiene-16-oic acid.

Since there are currently no product standards on the market, LCMS-IT-TOF ion fragments are used for judging product synthesis. Compared with a blank control group carrying pY26-GPD-TEF empty vector plasmid, a response value of a product peak is 1.9*10$^6$. The present disclosure has achieved de novo synthesis of 3,15,19-Trihydroxy-8 (17),13-ent-labdadiene-16-oic acid for the first time. This strategy provides necessary references for analyzing biosynthesis pathway of andrographolide and using metabolic engineering to synthesize andrographolide and related derivatives thereof.

DETAILED DESCRIPTION (I) Culture Medium

Figure 1:
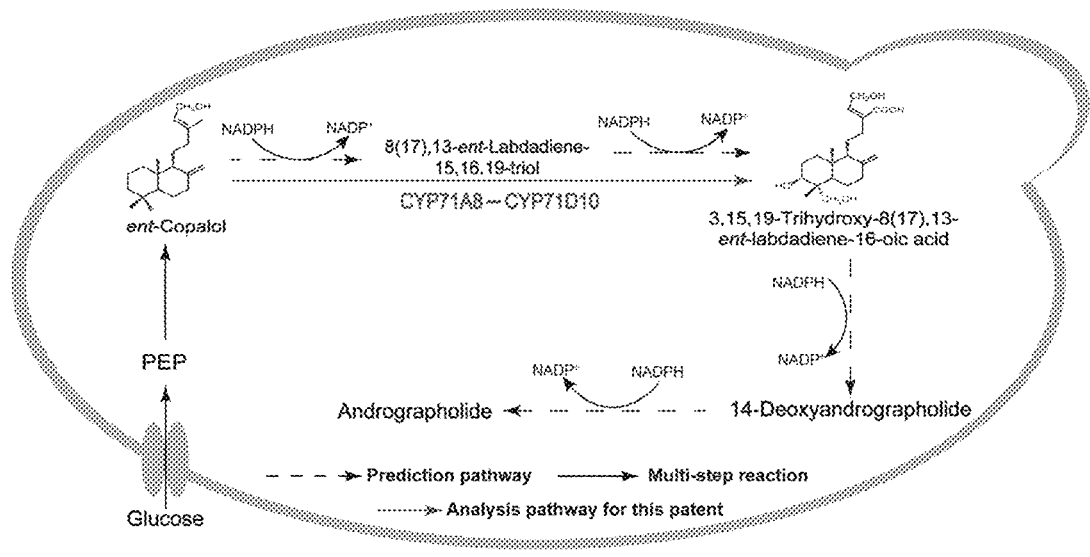
FIG. 1: Reaction diagram for catalytic synthesis of 3,15, 19-Trihydroxy-8(17),13-ent-labdadiene-16-oic acid by eukaryotic microorganisms.

LB medium: peptone 10 g/L, yeast powder 5 g/L, and sodium chloride 10 g/L. 20 g/L agar powder is added to prepare an LB solid culture medium.

YPD medium: peptone 20 g/L, yeast powder 10 g/L, and glucose 20 g/L. 20 g/L agar powder is added to prepare a YPD solid medium.

TB medium: peptone 12 g/L, yeast powder 24 g/L, dipotassium hydrogen phosphate 12.54 g/L, potassium dihydrogen phosphate 2.31 g/L, and glycerol 5 g/L.

YNB medium: glucose 20 g/L, and 20 mL/LYNB medium (purchased from Sangon Biotech (Shanghai) Co., Ltd.). 20 g/L agar powder is added to prepare a YNB solid medium.

(II) Strains and Plasmids pY26-GDP-TEF, pET22b(+), pET28a(+) and pMD-19 vectors are all commercial plasmids, *S. cerevisiae* CEN.PK2-1D is a commercial yeast cell, and chassis cell C800 is a publicly available strain, recorded in Promoter-Library-Based Pathway Optimization for Efficient (2S)-Naringenin Production From p-Coumaric Acid in *Saccharomyces cerevisiae*, Song Gao, Hengrui zhou, Jingwen Zhou, Jian chen. J Agric Food Chem, 2020 Jun. 24.

Figure 2:
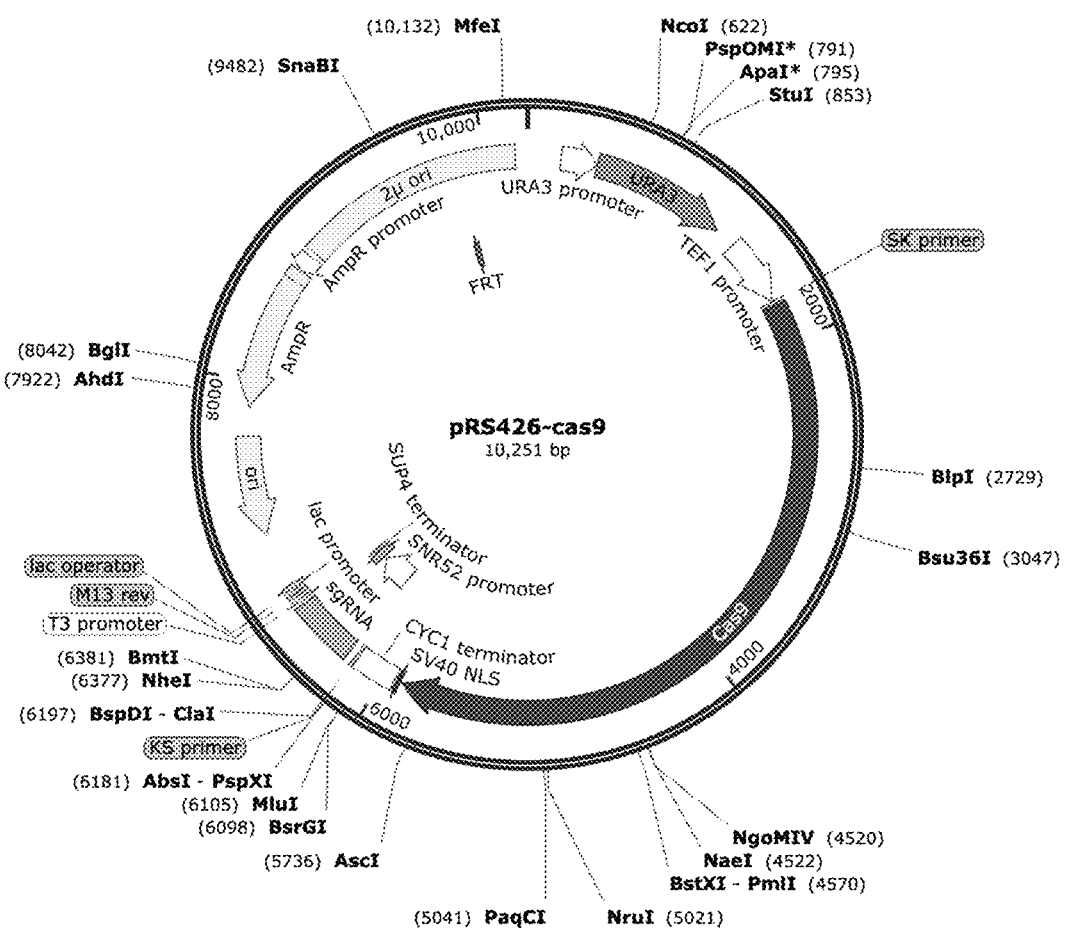
FIG. 2: Vector map of pRS426-TEF1-Cas9-gRNA-URA3.

A pRS426-TEF1-Cas9-gRNA-URA3 vector (SEQ ID NO:49) is synthesized by Jiangsu Genecefe Biotechnology Co., Ltd., and the vector map is shown in FIG. 2.

(III) 3,15,19-Trihydroxy-8(17),13-ent-labdadiene-16-oic Acid Detection Conditions Measurement is performed using LCMS-IT-TOF. Conditions: Chromatographic column C18 (4.6 mm×250 mm, 5 μm); mobile phase methanol (B)-water (A), gradient elution (0-24 min, 30-60% B; 24-40 min, 60% B; 40-46 min, 60%-30% B; 46-50 min, 30% B); column temperature 35° C.; flow rate 0.5 mL/min; and injection volume 5 μL.

Figure 3:
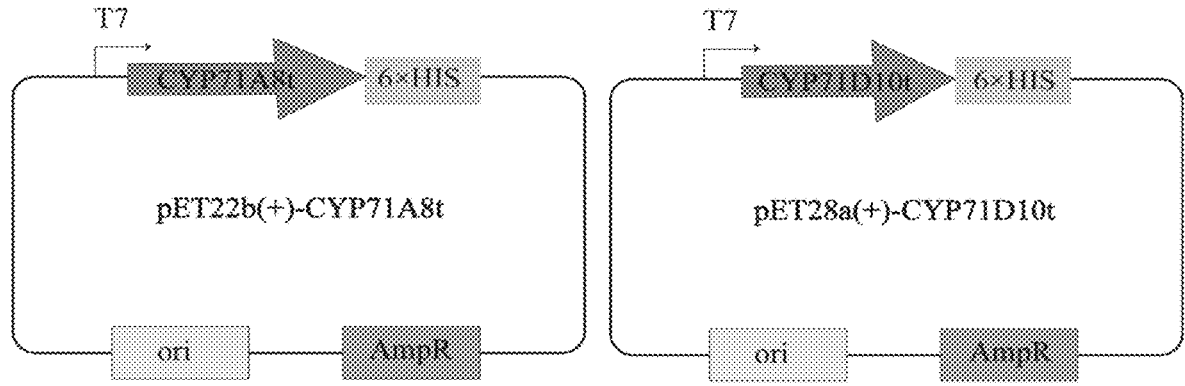
FIG. 3: Plasmid map of pET22b(+)-P$_{T7}$-CYP71A8t and pET28a(+)-P$_{T7}$-CYP71D10t.

Example 1 Construction of Recombinant Plasmids pET22b(+)-CYP71A8t and pET28a(+)-CYP71D10t Two original CYP450 enzymes CYP71A8 (a nucleotide sequence as shown in SEQ ID NO:1) and CYP71D10 (a nucleotide sequence as shown in SEQ ID NO:2) derived from *Andrographis paniculata* were used as templates respectively. PCR amplification was performed using primer pairs 71A8t-F/71A8t-R and 71D10t-F/71D10t-R to obtain target fragments CYP71A8t (a nucleotide sequence as shown in SEQ ID NO:3) and CYP71D10t (a nucleotide sequence as shown in SEQ ID NO:4) both with truncated signal peptides. The amplified CYP71A8t and CYP71D10t were verified by 1.5% agarose gel electrophoresis and then subjected to Gibson assembly with the pET22b(+) and pET28a(+) expression vectors respectively. The assembled plasmids were transferred into *E. coli* JM109 competent cells, spread on an LB solid medium containing corresponding antibiotics, and cultured at 37° C. overnight. Positive clones were selected and plasmids were extracted. After sequencing was correct, the plasmids were reserved for expression of recombinant *E. coli* BL21 (DE3) protein. The plasmids were named pET22b(+)-$P_{T7}$-CYP71A8t and pET28a(+)-$P_{T7}$-CYP71D10t respectively (plasmid map shown in FIG. 3).

TABLE 1

| Primers used for constructing CYP71A8t and CYP71D10t expression vectors | | |
| --- | --- | --- |
| Primer | Sequence (5'-3') | |
| 71A8t-F | CTGCCCAGCCGGCGATGGCCACCAAGAACTTGCCCCCGT | SEQ ID NO: 13 |
| 71A8t-R | CAGTGGTGGTGGTGGTGGTGAACGAACACACCCTCAGTATA GAACTTTG | SEQ ID NO: 14 |
| 71D10t-F | TAAGAAGGAGATATACCATGAAACGTCCCCGGAGTTCCG | SEQ ID NO: 15 |
| 71D10t-R | CAGTGGTGGTGGTGGTGGTGCTTTACAGGCAAAGGGTTTTT CAATTTGGG | SEQ ID NO: 16 |

Example 2 Heterologous Expression of CYP71A8t and CYP71D10t

After the plasmids pET22b(+)-$P_{T7}$-CYP71A8t and pET28a(+)-$P_{T7}$-CYP71D10t constructed in Example 1 were respectively transferred into *E. coli* BL21 competent cells, single clones were selected and inoculated into an LB medium containing 100 mg/L ampicillin and 50 mg/L kanamycin respectively, and cultured at 37° C. and 220 rpm for 16 h to serve as seed liquid. Then the seed liquid in a volume ratio of 1% inoculation amount was respectively transferred to a TB medium with ampicillin or kanamycin (50 mL medium in a 250 mL shaking flask, 50 g/L antibiotics, and 1/1000 volume ratio), and cultured at 37° C. and 220 rpm until $OD_{600}$ of fermentation broth reached 0.6-0.8. A final concentration of 80 mg/L 5-aminolevulinic acid hydrochloride, 10 mg/L $FeSO_4$ solution and 0.5 mM IPTG were added to induce expression of CYP71A8t and CYP71D10t proteins. After induction at 16° C. for 20 h, the cells were collected by centrifugation at 4° C. and 6000 rpm for 15 min.

Figure 4:
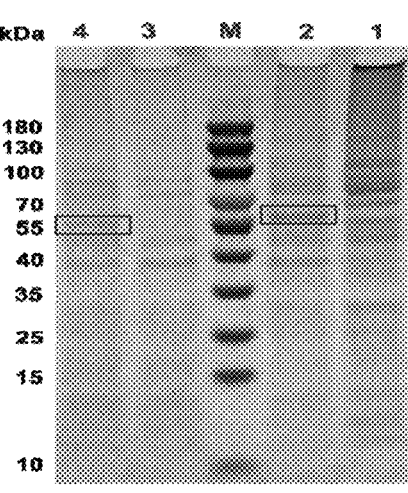
FIG. 4: SDS-PAGE diagram of BL21 (DE3) expressing CYP71A8t and CYP71D10t; 1: pET22b empty vector; 2: pET22b-CYP71A8t; M: Marker; 3: pET28a empty vector; and 4: pET28a-CYP71D10t.

After washing the collected cells twice with PBS buffer (pH=7.4), lysis buffer (500 mM potassium phosphate, pH 7.4, 250 mM NaCl, 0.25% sodium cholate, 10% glycerol, 10 mM imidazole, and 10 mM β-mercaptoethanol) was added to resuspend the cells. The cells were sonicated on ice for 3 minutes, and cell lysate was centrifuged at 4° C. and 10000 rpm for 20 min to remove cell debris. Supernatant was collected and subjected to SDS-PAGE protein verification (results shown in FIG. 4).

Example 3 Expression Identification of Recombinant Plasmids pET22b(+)-CYP71A8t57 and pET28a(+)-CYP71D10t59

Using original sequences of CYP71A8 and CYP71D10 as templates and using primers (Table 2), 57 and 59 amino acids were truncated respectively, and named CYP71A8t57 (a nucleotide sequence as shown in SEQ ID NO:5) and CYP71D10t59 (a nucleotide sequence as shown in SEQ ID NO:6). A method for constructing recombinant plasmids was the same as in Example 1, and the corresponding plasmids were named pET22-CYP71A8t57 and pET28-CYP71D10t59. Induction and identification methods were the same as in Example 2. Supernatant of lysate was collected. SDS-PAGE protein electrophoresis results showed that the protein was not expressed.

TABLE 2

Primers used for constructing CYP71A8t57 and CYP71D10t59 expression vectors

| Primer | Sequence (5'-3') | |
|---|---|---|
| 71A8t57-F | CACCAGCTGAGCTCATTGCCTCACCACGACCTCCGGC | SEQ ID NO: 17 |
| 71A8t57-R | CAGTGGTGGTGGTGGTGGTGAACGAACACACCCTCAGTATAGAAC TTTG | SEQ ID NO: 18 |
| 71D10t59-F | GTCAGCTCCCGACCACCGCATCATATTTTAGCCGACTTGGCGTC | SEQ ID NO: 19 |
| 71D10t59-R | CAGTGGTGGTGGTGGTGGTGCTTTACAGGCAAAGGGTTTTCAAT TTGGG | SEQ ID NO: 20 |

**Example 4 Construction of *S. cerevisiae* CW1006**

Using *S. cerevisiae* CEN.PK2-1D genome as a template, primer pairs 2UProx1-F/2UProx1-R and 7DOWNrox1-F/7DOWNrox1-R were used to amplify and obtain upstream and downstream homology fragments of ROX1 respectively, primer 3GAL7-F/3GAL7-R was used to amplify and obtain a promoter $P_{GAL7}$ fragment, and primer 5TEF1-F/5TEF1-R was used to amplify and obtain a promoter $P_{TEF1}$ fragment. Using *Andrographis paniculata* genome as a template, primer 4ApGGPPS-F/4ApGGPPS-R was used to amplify and obtain an ApGGPPs fragment, and primer 6ApCPS-F/6ApCPS-R was used to amplify and obtain an ApCPS fragment. Using pMD-19 vector as a template, primer 1GJ-F/1GJ-R was used to amplify and obtain a linearized fragment of vector pMD-19. The above fragments were purified and subjected to Gibson assembly to obtain vector pMD19T-UProx1-$P_{GAL7}$-ApGGPPs-$P_{TEF1}$-ApCPS-DOWNrox1. The obtained vector was transformed into *E. coli* JM109 and sequenced for verification, and positive recombinant vector pMD19T-UProx1-$P_{GAL7}$-ApGGPPs-$P_{TEF1}$-ApCPS-DOWNrox1 was obtained. Using the above vector as a template, primer 2UProx1-F/7DOWNrox1-F was used to amplify and obtain a Donar-ROX1 fragment.

Using pRS426-TEF1-Cas9-gRNA-URA3 vector as a template, primer Cas9-F/Cas9-R was used to amplify and obtain linearized vector pRS426-TEF1-Cas9-gRNA-URA3. The obtained vector was transformed into *E. coli* JM109 and sequenced for verification. Recombinant vector pRS426-20nt with a correct sequence was obtained.

The above Donar-ROX1 fragment and pRS426-20nt were transformed into chassis cell C800, spread on YNB solid plates (containing 50 mg/L Leu, His and Trp), and cultured at 30° C. for 2-3 days. Positive clone strains were selected and passaged multiple times, then pRS426 plasmid was lost (cells can grow on YPD solid plates, but cannot grow on the YNB solid plates containing 50 mg/L Leu, His and Trp), and the CW1006 strain was successfully constructed.

TABLE 3

| Primers used for constructing CW1006 strain | | |
| --- | --- | --- |
| Primer | Sequence (5'-3') | |
| 1GJ-F | gaatttgacaatgttaagctttgttaaacagcttggcgtaatcatggtcatag ctgtt | SEQ ID NO: 21 |
| 1GJ-R | ggtagttccacgcggccgatccgagttctaattcactggccg | SEQ ID NO: 22 |
| 2UProx1-F | ggccagtgaattagaactcggatcggccgcgtggaactac | SEQ ID NO: 23 |
| 2UProx1-R | aaggatagtaagctggcaaatgttgattgtctaactgcgttcttttgt | SEQ ID NO: 24 |
| 3GAL7-F | aagaacgcagttagacaatcaacatttgccagcttactatccttcttgaaaat atg | SEQ ID NO: 25 |
| 3GAL7-R | AATTTTGGAGAAACGTCGGttttgagggaatattcaactgttttttttt atcatgttga | SEQ ID NO: 26 |
| 4ApGGPPS-F | agttgaatattccctcaaaaCCGACGTTTCTCCAAAATTCATTTCA ATTTTTTC | SEQ ID NO: 27 |
| 4ApGGPPS-R | tagaaacattttgaagctatTCAATTCTGCCTCCGACCAATGTAC | SEQ ID NO: 28 |
| 5TEF1-F | ATTGGTCGGAGGCAGAATTGAatagcttcaaaatgtttctactcctt ttttactcttc | SEQ ID NO: 29 |
| 5TEF1-R | AGGAGGGAAAACAAAGGCATcttagattagattgctatgctttcttt ctaatgagc | SEQ ID NO: 30 |
| 6ApCPS-F | gcatagcaatctaatctaagATGCCTTTGTTTTCCCTCCTCG | SEQ ID NO: 31 |
| 6ApCPS-R | gcataaatttttagttaaagggTCAGAAGTAACGGCGGGTATGGT C | SEQ ID NO: 32 |
| 7DOWNrox1-F | CATACCCGCCGTTACTTCTGAccctttaactaaaaatttatgcatttg gctcc | SEQ ID NO: 33 |
| 7DOWNrox1-R | tatgaccatgattacgccaagctgtttaacaaagcttaacattgtcaaattctt cagg | SEQ ID NO: 34 |
| Cas9-F | TGTTAATACTTCTAACTATAgtttttagagctagaaatagcaagttaaa ataaggctag | SEQ ID NO: 35 |
| Cas9-R | TATAGTTAGAAGTATTAACAgatcatttatctttcactgcggagaagtt tc | SEQ ID NO: 36 |

Figure 5:
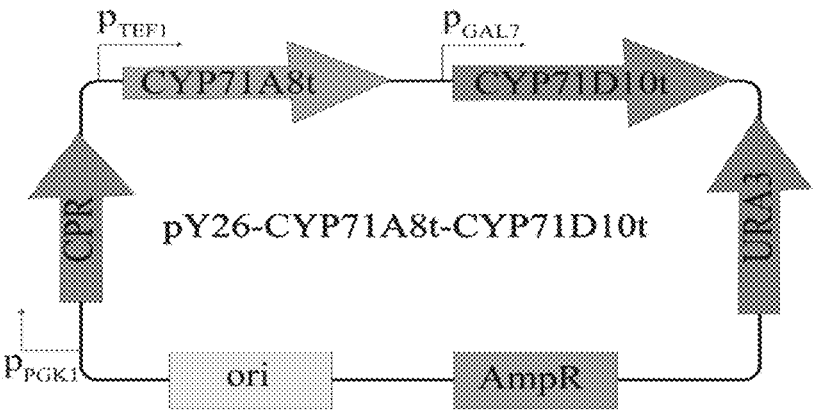
FIG. 5: Plasmid map of pY26-P$_{TEF1}$-CYP71A8t-P$_{GAL7}$-CYP71D10ts.

Example 5 Construction of Eukaryotic Microorganism Expression System for CYP71A8t and CYP71D10t Using *Andrographis paniculata* genome as a template, primer CPR-F/CPR-R was used to amplify ApCPR gene. Using *S. cerevisiae* genome as a template, primer P$_{GAL7}$-F/P$_{GAL7}$-R was used to amplify promoter P$_{GAL7}$, and primer PTEF1-F/PTEF1-R was used to amplify promoter P$_{TEF1}$. Using a nucleotide sequence of CYP71A8 as a template, primer CYP71A8t-F/CYP71A8t-R was used to amplify CYP71A8t. Using a nucleotide sequence of CYP71D10 as a template, primer CYP71D10t-F/CYP71D10t-R was used to amplify CYP71D10t. Using expression vector pY26-GDP-TEF as a template, primer pY26-F/pY26-R was used to amplify a linearized vector. The amplified products were recovered by ethanol precipitation. The promoter P$_{GAL7}$, promoter P$_{TEF1}$, CYP71A8t, CYP71D10t and linearized vector were subjected to Gibson assembly to obtain a recombinant vector. The recombinant vector was transferred into *E. coli* JM109 competent cells, spread on an LB solid medium containing 100 mg/L ampicillin, and cultured at 37° C. overnight. Positive clones were selected and plasmids were extracted. Correctly sequenced plasmids were transferred into the *S. cerevisiae* CW1006 constructed in Example 4, spread on YNB solid plates (containing 50 mg/L Leu, His and Trp), and cultured at 30° C. for 2-3 days. Positive clones were selected, and recombinant *S. cerevisiae* CW1006/pY26-P TEF1-CYP71A8t-P$_{GAL7}$-CYP71D10t was constructed (plasmid map shown in FIG. 5).

TABLE 4

| Primers used for constructing pY26-P$_{TEF1}$-CYP71A8t-P$_{GAL7}$-CYP71D10t expression vector | | |
| --- | --- | --- |
| Primer | Sequence (5'-3') | |
| CPR-F | GTAAAGGGGGSGGGGSGGGGSATGGATTCGCGGCTGGAG | SEQ ID NO: 37 |
| CPR-R | gaatgtaagcgtgacataacTCACCAAACATCCCTCAGGTATCG | SEQ ID NO: 38 |
| PGAL7-F | accaaacctctggcgaagaatttgccagcttactatccttcttgaaa | SEQ ID NO: 39 |

TABLE 4-continued

Primers used for constructing pY26-P$_{TEF1}$-CYP71A8t-P$_{GAL7}$-CYP71D10t expression vector

| Primer | Sequence (5'-3') | |
|---|---|---|
| PGAL7-R | GGGGGCAAGTTCTTGGTCATttttgagggaatattcaactgttttttttttat catgttg | SEQ ID NO: 40 |
| CYP71A8t-F | agttgaatattccctcaaaaATGACCAAGAACTTGCCCCC | SEQ ID NO: 41 |
| CYP71A8t-R | cattttgaagctatgagctcAACGAACACACCCTCAGTATAGAACTTT G | SEQ ID NO: 42 |
| PTEF1-F | CAAAGTTCTATACTGAGGGTGTGTTCGTTgagctcatagcttcaaaat gtttctactcctt | SEQ ID NO: 43 |
| PTEF1-R | GAACTCCGGGGACGTTTCATactagttctagaaaacttagattagattgc tatgctttc | SEQ ID NO: 44 |
| CYP71D10t-F | ctaagttttctagaactagtATGAAACGTCCCCGGAGTTCC | SEQ ID NO: 45 |
| CYP71D10t-R | ATCCATSCCCCSCCCCSCCCCCTTTACAGGCAAAGGGTTTTCA ATTTGG | SEQ ID NO: 46 |
| pY26-F | ACCTGAGGGATGTTTGGTGAgttatgtcacgcttacattcacgcc | SEQ ID NO: 47 |
| pY26-R | aaggatagtaagctggcaaattcttcgccagaggtttggtc | SEQ ID NO: 48 |

Example 6 Synthesis of 3,15,19-Trihydroxy-8(17),13-ent-labdadiene-16-oic Acid by Recombinant *S. cerevisiae*

Figure 6:
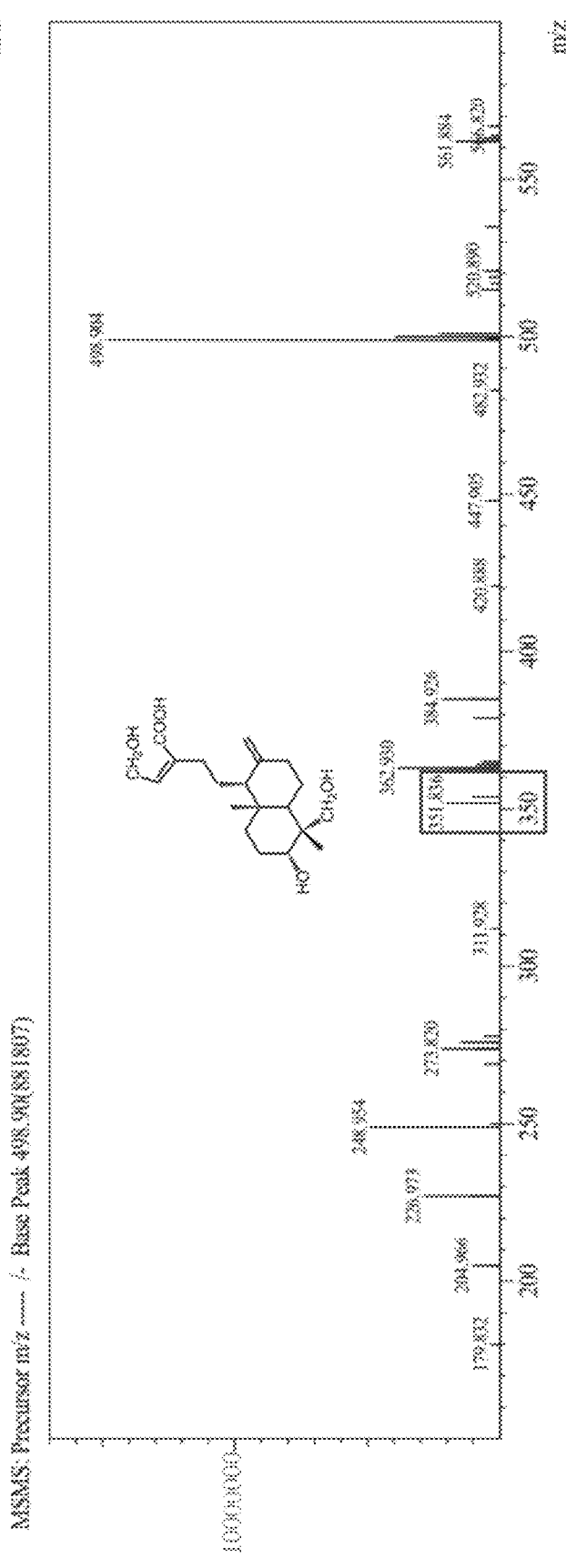
FIG. 6: LCMS-IT-TOF ion chromatogram of recombinant *S. cerevisiae* catalyzing ent-Copalol to synthesize 3,15,19-Trihydroxy-8(17),13-ent-labdadiene-16-oic acid.

The recombinant *S. cerevisiae* CW1006/pY26-P$_{TEF1}$-CYP71A8t-P$_{GAL7}$-CYP71D10t constructed in Example 5 was streaked and inoculated into an LB medium containing 50 mg/L ampicillin, and cultured at 37° C. overnight. Single colonies were selected and transferred into an YNB medium (containing 50 mg/L Leu, His and Trp), and cultured at 30° C. and 220 rpm for 16-18 h. The culture was transferred to a fresh 25 mL YPD medium at a 1% (v/v) inoculation amount, and cultured at 30° C. and 220 rpm. After fermen-tation for 120 h, fermentation broth was collected, and a response value of 3,15,19-Trihydroxy-8(17),13-ent-labdadi-ene-16-oic acid was measured by LCMS-IT-TOF. The results were shown in FIG. 6. A response value of a product peak reached 1.9*106.

Although the present disclosure has been disclosed in exemplary embodiments above, it is not intended to limit the scope of the present disclosure. Those skilled in the art can make various changes and modifications within the spirit and scope of the present disclosure, and therefore the scope of protection of the present disclosure should be defined by the claims.

10

What is claimed is:

1. A recombinant *Saccharomyces cerevisiae*, comprising knockout of ROX1 and GAL80 genes on the genome; integrative expression of a GGPP synthase encoding gene and CPS diterpene synthase encoding gene; and free expression of CYP71A8 encoding gene CYP71A8t with N-terminal truncated by 32 amino acids, CYP71A10 encoding gene CYP71D10t with N-terminal truncated by 28 amino acids, and CPR encoding gene ApCPR;

wherein a nucleotide sequence of the CYP71A8 with N-terminal truncated by 32 amino acids is set forth in SEQ ID NO:3 and a nucleotide sequence of the CYP71D10 with N-terminal truncated by 28 amino acids being shown in SEQ ID NO:4; a nucleotide sequence of the ApCPR is set forth in SEQ ID NO:7; a nucleotide sequence of the GGPP synthase is set forth in SEQ ID NO:8; and a nucleotide sequence of the CPS diterpene synthase is set forth in SEQ ID NO:9.

2. The recombinant *S. cerevisiae* according to claim 1, wherein after the knockout of ROX1 site, the GGPP syn-thase encoding gene and the CPS diterpene synthase encoding gene are integrated at the ROX1 site.

3. The recombinant *S. cerevisiae* according to claim 1, wherein promoter $P_{PGK1}$ is used for starting expression of the CPR encoding gene; promoter PTEF1 is used for starting expression of the CYP71A8t; and promoter $P_{GAL7}$ is used for starting expression of the CYP71D10t.

4. A whole-cell catalyst, containing the recombinant *S. cerevisiae* according to claim 1.

5. A method for synthesizing 3,15,19-Trihydroxy-8 (17), 13-ent-labdadiene-16-oic acid, using the recombinant *S. cerevisiae* according to claim 1 comprising the recombinant *S. cerevisiae* as a fermentation strain for fermentation to produce 3,15,19-Trihydroxy-8(17),13-ent-labdadiene-16-oic acid.

6. A method for synthesizing 3,15,19-Trihydroxy-8(17), 13-ent-labdadiene-16-oic acid, using the whole-cell catalyst of claim 4 comprising the recombinant *S. cerevisiae* as a fermentation strain for fermentation to produce 3,15,19-Trihydroxy-8(17),13-ent-labdadiene-16-oic acid.

* * * * *

SEQUENCE LISTING

```
Sequence total quantity: 49
SEQ ID NO: 1          moltype = DNA  length = 1527
FEATURE               Location/Qualifiers
source                1..1527
                      mol_type = other DNA
                      organism = synthetic construct
SEQUENCE: 1
atggatgcaa tagtattcca cccctatgtt ttccaagccc ttggatctct cctcatctta   60
tggctgattt caaaatggtt caacaaatcc aatggaacca agaacttgcc cccgtcaccg  120
ccgatgctcc cgataatcgg aaacctccac cagctgagct cattgcctca ccacgacctc  180
cggcgcttgg cgcgcaaaca tggtcctctc atgctgctgc actttggcac cgtgcctacg  240
ctcatcgtgt catccgtgga gggcgccaag gaaataatga aaactcatga tcttgcattt  300
gcagaccggc ccgagtcttg ggttactaag aggctgctct acgatcacaa ggatgtgtcg  360
gttgcgccgt atggcgaata ttggagacag ttgaagagta tatgtgtgct ccagcttctc  420
agcaataaaa gagtccaatc tttccattcg atccgggaag aagaaatgtc ccttttgatg  480
gaaaaaatta ggggctcgtc acgcgcgttg aatttgagtg agatgttcac taaagtcact  540
aatgatatg tttgtagatc ggcgtttggt gtgaaatacg gcgagggaga aaaggggaag  600
aaattcatgg cgcttttgac ggagtttttg gagttgttag ggaccattta catcggaaat  660
tttgtgccgt ggctttcgtg gattactcgt cttaccgggt tcgatgcaag agtggataag  720
gttgcaaaag agctcgacat attgatggag gatgtgatcg aagaaaggat tagaagaaat  780
cttgaagata aggctgagaa tgaacacaag tatggacaaa attttgtaga tattttggta  840
gatatttaca agaacaattc tgcaggcatc tccatggaca gagatagtgt gaaagcaata  900
ctttttggatg tttttgcagc tgggacggac accacatcga ctgttctaga atgggcgatg  960
agtgaactcc ttcgacaccc cgaggtgatg aagaaactgc aaaatgaagt gaggggagta 1020
atgaaagaca agggcaagat aagcgatgaa gacttagaaa aaatgcaata tctaaaagcc 1080
gtgatcaaag aaactcttcg cctgcacact ccgatcccag ctctagttcc tcggatggca 1140
agaaaagatg tcaaggttat gggatacgat gtatcagccg ggacaatggt gatgattaat 1200
gcttgggcca taggcagaga ccccggcatt tgggatgagc ctgaaaagtt caaccctaac 1260
cggtttctaa attcatcgat agatttcaag ggccaggatt tcgagctgat cccttttggg 1320
```

```
gccgggcggc gaggctgccc ggggatttca tttgctatgg ctaccaatga gtttgtgtta   1380
gcaaatattg tgcataactt caagtggaaa ttggctgatg atgagaaaga attagacatg   1440
agtgaacgcc ccggtgtcgc cattcgtagg gctgttcctc ttcttgccgt ggcatcaaag   1500
ttctatactg agggtgtgtt cgtttga                                       1527

SEQ ID NO: 2            moltype = DNA  length = 1515
FEATURE                 Location/Qualifiers
source                  1..1515
                        mol_type = other DNA
                        organism = synthetic construct
SEQUENCE: 2
atggatcgtg atttcttatc ttctattatc ctttttcctt ctctcatatt tcttgcattc   60
ttatggaatc taatcactcg ctccaaacgt ccccggagtt ccggcgaact tccgccgggg   120
ccgagaaagc tgccggtcat cgggaacttg cacaaccttg tcagctcccg accaccgcat   180
catatttag ccgacttggc gtcgaaatat ggggcgatga tgcacttgcg gctaggtgaa   240
atcagcacgg ttgttatatc gtcgccggag gcagcaaaag aggtcatgaa gacatatgac   300
atcaacttcg ctaataggcc atctttctat gcatcgaaga ttataactta tgacaactcc   360
gacataggat tctccaatgg agaataccgg aaaaatttgc gaaaagtaag caaaatggag   420
ctgctgagtg cgaagcgcgt caaatctttt cgtcccttaa gggaagaagt gttttcggat   480
atgtgcagtt ggatagcttc aaaagaaggc tcgtcgataa acttgactga gaaagtttcc   540
ttggcgactt ttgatgtggc tttgcgggca tcgcttggcg gaaagattga tgaacacaca   600
gcaatggtag atgtaactaa ggagtctttc gatttactcg caggatttta tgccggcgat   660
ttgtttccct ccatcagttt gttgcaatca atcgacggat ttagaggtcg tgtggagaag   720
gtgcacaaac tatccgatgc catactccag aagattattg acagtcgaaa agtagccaaa   780
tctcaaggca aaacacacga aaacttggtt gatattctcc tcaaattcca taaggatacc   840
gggcatgatc tcggcttaag cgatgacaat ataaaagctg tgctacagga tatgttcatt   900
gctggaatcg aaacatcatc gacaactaca gattgggcca tggcagaaat gatgaaacat   960
ccaagccttc ttaagaaggc acaagatgag gtgagacaga ttttttctcga caagggattt  1020
gtcgatgagt ccgacttcga tgagctaaag tacctaaact tagtgatcaa agaaactttc   1080
cgaatccacc cgccggggcc tttaattctc agagaaaaca aagagacctg tgagatcaat   1140
ggatacacaa tacctgcaaa aacaaggggt gtggtgaatg catgggccat tggaagagat   1200
cccaaaatct ggaaagatgc cgacagcttt ataccagaga gatttctcga taacaatatt   1260
tcagccgatt cactggaaa gaatttcgat tacatccctt ttggctctgg tcgaaggatt   1320
tgccctggaa tgtcattcgg catagctaac gtcgaattcc cattggcaat gttactctac   1380
cacttcgatt gggttttgcc acaggaatc aaacctgaag atgtggacat ggctgaatcc   1440
tttggcctta cagcagtaag aaaaactcct cttactgtga ttcccaaatt gaaaaaccct   1500
ttgcctgtaa agtaa                                                    1515

SEQ ID NO: 3            moltype = DNA  length = 1431
FEATURE                 Location/Qualifiers
source                  1..1431
                        mol_type = other DNA
                        organism = synthetic construct
SEQUENCE: 3
accaagaact tgcccccgtc accgccgatg ctcccgataa tcggaaacct ccaccagctg   60
agctcattgc ctcaccacga cctccggcgc ttggcgcgca aacatggtcc tctcatgctg   120
ctgcactttg gcaccgtgcc tacgctcatc gtgtcatccg tggggggcgc caaggaaata   180
atgaaaactc atgatcttgc atttgcagac cggcccgagt cttgggttac taagaggctg   240
ctctacgatc acaaggatgt gtcggttgcg ccgtatggcg aatattggag acagttgaag   300
agtatatgtg tgctccagct tctcagcaat aaaagagtcc aatctttcca ttcgatccgg   360
gaagaagaaa tgtcccttt gatggaaaaa attagggcgt cgtcacgcgc gttgaatttg   420
agtgagatgt tcactaaagt cactaatgat atggtttgta gatcggcgtt tggtgtgaaa   480
tacggcgagg gagaaaaggg gaagaaattc atggcgcttt tgacggagtt tttgagttg   540
ttagggacca tttacatcgg aaattttgtg ccgtggcttt cgtggattac tcgtcttacc   600
gggttcgatg caagagtgga taaggttgca aaagagctcg acatattgat ggaggatgtg   660
atcgaagaaa ggattagaag aaatcttgaa gataaggctg agaatgaaca caagtatgga   720
caaaattttg tagatatttt ggtagatatt tacaagaaca attctgcagg catctccatg   780
gacagagata gtgtgaaagc aatacttttg gatgttttg cagctgggac ggacaccaca   840
tcgactgttc tagaatgggc gatgagtgaa ctccttcgac accccgaggt gatgaagaaa   900
ctgcaaaatg aagtgagggg agtaatgaaa gacaaggca agataagcga tgaagactta   960
gaaaaaatgc aatatctaaa agccgtgatc aaagaaactc ttcgcctgca cactccgatc  1020
ccagctctag ttcctcggat ggcaagaaaa gatgtcaagg ttatgggata cgatgtatca  1080
gccgggacaa tggtgatgat taatgcttgg gccataggca gagaccccgg catttgggat  1140
gagcctgaaa agttcaaccc taaccggttt ctaaattcat cgatagattt caagggccag  1200
gatttcgagc tgatcccttt tggggccggg cggcgaggct gcccgggat ttcatttgct  1260
atggctacca atgagtttgt gttagcaaat attgtgcata acttcaagtg gaaattggct  1320
gatgatgaga agaattaga catgagtgaa cgccccggtg tcgccattcg tagggctgtt  1380
cctcttcttg ccgtggcatc aaagttctat actgagggtg tgttcgtttg a           1431

SEQ ID NO: 4            moltype = DNA  length = 1430
FEATURE                 Location/Qualifiers
source                  1..1430
                        mol_type = other DNA
                        organism = synthetic construct
SEQUENCE: 4
aaacgtcccc ggagttccgg cgaacttccg ccggggccga aaagctgcc ggtcatcggg   60
aacttgcaca accttgtcag ctcccgacca ccgcatcata ttttagccga cttggcgtcg   120
aaatatgggg cgatgatgca cttgcggcta ggtgaaatca gcacggttgt tatatcgtcg   180
ccggaggcag caaaagaggt catgaagaca tatgacatca acttcgctaa taggccatct   240
```

```
ttctatgcat cgaagattat aacttatgac aactccgaca taggattctc caatggagaa    300
taccggaaaa atttgcgaaa agtaagcaaa atggagctgc tgagtgcgaa gcgcgtcaaa    360
tcttttcgtc ccttaaggga agaagtgttt tcggatatgt gcagttggat agcttcaaaa    420
gaaggctcgt cgataaactt gactgagaaa gtttccttgg cgacttttga tgtggctttg    480
cgggcatcgc ttggcggaaa gattgatgaa cacacagcaa tggtagatgt aactaaggag    540
tctttcgatt tactcgcagg attttatgcc ggcgatttgt ttccctccat cagtttgttg    600
caatcaatcg acggatttag aggtcgtgtg gagaaggtgc acaaactatc cgatgccata    660
ctccagaaga ttattgacag tcgaaaagta gccaaatctc aaggcaaaac acacgaaaac    720
ttggttgata ttctcctcaa attccataag gataccgggc atgatctcgg cttaagcgat    780
gacaatataa aagctgtgct acaggatatg ttcattgctg gaatcgaaac atcatcgaca    840
actacagatt gggccatggc agaaatgatg aaacatccaa gccttcttaa gaaggcacaa    900
gatgaggtga gacagatttt tctcgacaag ggatttgtcg atgagtccga cttcgatgag    960
ctaaagtacc taaacttagt gatcaaagaa actttccgaa tccacccgcc ggggcctta   1020
attctcagag aaaacaaaga gacctgtgag atcaatgaat acacaataac tgcaaaaaca   1080
agggttgtgg tgaatgcatg ggccattgga agagatccca aaatctggaa agatgccgac   1140
agctttatac cagagagatt tctcgataac aatatttcag ccgattacac tggaaagaat   1200
ttcgattaca tcccttttgg ctctggtcga aggatttgcc ctggaatgtc attcggcata   1260
gctaacgtcg aattcccatt ggcaatgtta ctctaccact tcgattgggt tttgccacag   1320
ggaatcaaac ctgaagatgt ggacatggct gaatcctttg gccttacagc agtaagaaaa   1380
actcctctta ctgtgattcc caaattgaaa aacccctttgc ctgtaaagta            1430

SEQ ID NO: 5             moltype = DNA   length = 1359
FEATURE                  Location/Qualifiers
source                   1..1359
                         mol_type = other DNA
                         organism = synthetic construct
SEQUENCE: 5
caccacgacc tccggcgctt ggcgcgcaaa catggtcctc tcatgctgct gcactttggc     60
accgtgccta cgctcatcgt gtcatccgtg gagggcgcca aggaaataat gaaaactcat    120
gatcttgcat ttgcagaccg gcccgagtct tgggttacta agaggctgct ctacgatcac    180
aaggatgtgt cggttgcgcc gtatggcgaa tattggagac agttgaagag tatatgtgtg    240
ctccagcttc tcagcaataa aagagtccaa tctttccatt cgatccggga agaagaaatg    300
tcccttttga tggaaaaaat taggggctcg tcacgcgcgt tgaatttgag tgagatgttc    360
actaaagtca ctaatgatat ggtttgtaga tcggcgtttg gtgtgaaata cggcgaggga    420
gaaaagggga agaaattcat ggcgcttttg acggagtttt tggagttgtt agggaccatt    480
tacatcggaa attttgtgcc gtggctttcg tggattactc gtcttaccgg gttcgatgca    540
agagtggata aggttgcaaa agagctcgac atattgatgg aggatgtgat cgaagaaagg    600
attagaagaa atcttgaaga taaggctgag aatgaacaca agtatggaca aaattttgta    660
gatattttta tagatattta caagaacaat tctgcagatca tctccatgga cagagatagt    720
gtgaaagcaa tacttttgga tgtttttgca gctgggacgg acaccacatc gactgttcta    780
gaatgggcga tgagtgaact ccttcgcacc cccgaggtga tgaagaaact gcaaaatgaa    840
gtgaggggag taatgaaaga caaggcaag ataagcgatg aagacttaga aaaaatgcaa    900
tatctaaaag ccgtgatcaa agaaactctt cgcctgcaca ctccgatccc agctctagtt    960
cctcggatgg caagaaaaga tgtcaaggtt atgggatacg atgtatcagc cgggacaatg   1020
gtgatgatta atgcttgggc cataggcaga gaccccggca tttgggatga gcctgaaaag   1080
ttcaacccta accggtttct aaattcatcg atagatttca agggccagga tttcgagctg   1140
atccctttg gggccgggcg gcgaggctgc ccggggattt catttgctat ggctaccaat   1200
gagtttgtgt tagcaaatat tgtgcataac ttcaagtgga aattggctga tgatgagaaa   1260
gaattagaca tgagtgaacg ccccggtgtc gccattcgta gggctgttcc tcttcttgcc   1320
gtggcatcaa agttctatac tgagggtgtg ttcgtttga                          1359

SEQ ID NO: 6             moltype = DNA   length = 1338
FEATURE                  Location/Qualifiers
source                   1..1338
                         mol_type = other DNA
                         organism = synthetic construct
SEQUENCE: 6
catcatattt tagccgactt ggcgtcgaaa tatggggcga tgatgcactt gcggctaggt     60
gaaatcagca cggttgttat atcgtcgccg gaggcagcaa aagaggtcat gaagacatat    120
gacatcaact tcgctaatag gccatctttc tatgcatcga agattataac ttatgacaac    180
tccgacatag gattctccaa tggagaatac cggaaaaatt gcgaaaagt aagcaaaatg    240
gagctgctga gtgcgaagcg cgtcaaatct tttcgtccct taagggaaga agtgttttcg    300
gatatgtgca gttggatagc ttcaaaagaa ggctcgtcga taaacttgac tgagaaagtc    360
tccttggcga cttttgtgt ggctttgcgg gcatcgcttg gcggaaagat tgatgaacac    420
acagcaatgg tagatgtaac taaggagtct ttcgatttac tcgcaggatt ttatgccggc    480
gatttgtttc cctccatcag tttgttgcaa tcaatcgacg gatttagagg tcgtgtggag    540
aaggtgcaca aactatccga tgccatactc cagaagatta ttgacagtcg aaaagtagcc    600
aaatctcaag gcaaaacaca cgaaaacttg gttgatattc tcctcaaatt ccataaggat    660
accgggcatg atctcggctt aagcgatgac aatataaaag ctgtgctaca ggatatgttc    720
attgctggaa tcgaaacatc atcgacaact acagattggg ccatggcaga aatgatgaaa    780
catccaagcc ttcttaagaa ggcacaagat gaggtgagac agatttttct cgacaaggga    840
tttgtcgatg agtccgactt cgatgagcta aagtacctaa acttagtgat caaagaaact    900
ttccgaatcc acccgccggg gcctttaatt ctcagagaaa acaaagagac ctgtgagatc    960
aatggataca caatacctgc aaaaacaagg gttgtggtga atgcatgggc cattggaaga   1020
gatcccaaaa tctggaaaga tgccgacagc tttataccag agagatttct cgataacaat   1080
atttcagccg attacactgg aaagaatttc gattacatcc cttttggctc tggtcgaagg   1140
atttgccctg gaatgtcatt cggcatagct aacgtcgaat cccattggc aatgttactc   1200
taccacttcg attgggtttt gccacaggga tcaaacctg aagatgtgga catggctgaa   1260
tcctttggcc ttacagcagt aagaaaaact cctcttactg tgattcccaa attgaaaaac   1320
```

```
cctttgcctg taaagtaa                                                        1338

SEQ ID NO: 7             moltype = DNA   length = 2070
FEATURE                  Location/Qualifiers
source                   1..2070
                         mol_type = other DNA
                         organism = synthetic construct
SEQUENCE: 7
atggattcgc ggctggagct gttgagatcc gtcgagcaag cccttggggt caagctcggg    60
gacgagactg tggtgttggt gcttaccacc tcagtagccg tgattttggg gctgctcgtc    120
tttcttttgga agagatcggg cgataataga agcaaggatg ccaggcaggt cgtcgttccc   180
aagccggtct cgctcaagga cgacgacgag gacgaatatg tggggccaga caagaccaag    240
ctcaccatct tcttcgggac gcagaccggc accgccgagg gattcgctaa ggcattagcc    300
gaagagatca aggcaagata tgataaggcg gttgttaaca ttgtggacat ggatgattat   360
gctcaagatg acgaccaata cgaggaaaag ctgaagaaag agactctagc attttttcatg   420
gtcgctactt atggagatgg tgagccaact gataatgctg ctagatttta taaatggttc    480
actgaggggg aagaaagaga accctggctt cagcagcttt cctatggaat atttggtttg    540
ggtaatcgac aatatgaaca ttttaacaag attggaaagt tcattgatga gaagcttagt    600
gagcaaggtg caaaacgtct ggtacaacta ggtctaggag atgatgatca atgcatcgaa    660
gatgatttca ctgcctggaa agagcaacta tggcctgaat tagatcaaat tctgaggggt    720
gaagaaagtt tggactctgt ctctacccct tatacagctg caataccaga atatagagtt    780
gtgatccatg atgctgctat tccatcttat gatgacaatc atgcatttgt tgctaatgg    840
gatgcttcat atgatcttca tcacccttgc agagtcaatg ttgctgttca gagagaactt    900
cacacccctg aatctgaccg ttcatgtata catctggagt ttgacatatc tggaactggt    960
atagtatatg agactggaga tcatgttggt gttttttgctg aaaattgcga tgaaactgtc   1020
gaagaagcat ctaaactatt gggacagcct ttggatttac tattttccat ccactctgac   1080
aaggatgatg gctctccaat tggaggttca ttaccacctc catttcctgg cccctgcaca   1140
cttcgttctg cactggcaca ccacgctgac ctgttgaatc cacctcgaaa ggctgctttg   1200
actgcattag ccgcacatgc ttctgaaacc aatgaagctg aaaagcttaa attcttggca   1260
tccctcagg gaaaggatga gtatgcacaa tgggttgttg gcagtcagag aagtctcctt   1320
gaggtaatgg ctgagtttcc ttcttcaaaa cctccacttg gggtatttttt tgctgcaatt   1380
gctccacgtc tgcagccacg ctactattct atatcttcat ctccaaggtt tgccccaact   1440
cgtgttcatg tgacatgtgc tctagtttat ggtccaagtc cgactggccg aattcataaa   1500
ggagtgtgtt cgacctggat gaagcatgca gttcccttgg agaaaagcag tagctgtagc   1560
tgggctccta tttttatcag gccatcgaat ttcaaattgc ctgctgattc ttctattcca   1620
attgtcatgg tgggtcctgg aacagggttg gcaccttttta gaggattttt acaggaaaga   1680
atggctctga aaaatgacgg cgctcaactt gggcctgctc tattttttttt tggttgtagg   1740
aaccgccgtc aggattttat ttatgaaaat gagctgaatg attttgtgga tcaaggagta   1800
atatccgagc tgattgttgc attctcaagg gagggacaac aaaaggaata tgttcaacat   1860
aagatgctgg aaaaggcaga tcaagtttgg agtttgatct ctcagaaagg atatctctat   1920
gtgtgtggag atgcaaaggg gatggcgaga gatgttcatc gtacattgca caccatcgtc   1980
caaacgcagg aaaatgtcga ttcatcaaag gcagagtcta tagttaagaa acttcagatg   2040
gatggccgat acctgaggga tgtttggtga                                     2070

SEQ ID NO: 8             moltype = DNA   length = 1170
FEATURE                  Location/Qualifiers
source                   1..1170
                         mol_type = other DNA
                         organism = synthetic construct
SEQUENCE: 8
ccgacgtttc tccaaaattc atttcaattt tttctatccc aatttcacaa aacaattccg    60
acaatgggat caatgaatct cgtagacacc tgcgccgcca attccgccgc catttttccgg   120
ccggcgccgc caattcttcg gagcgccttc gtcggcgccg ccagactgcc gccgtgtcca   180
atccgactga aaaaaacgag cattgcgcat tccggcggcg tggcggcgat tctgacggag   240
gaggacgtga aactcgccgc cgggaaggag gggcggcagg aattcgactt cggccggtac   300
gtggcggaga aggcggagtt cgttaacgga gctctcgacg gcgccgtcgt gatgaggcag   360
ccggcggtga tccacgaggc gatgaggtac tcgttgctcg ccggcgggaa gcggatccgg   420
ccgatgctgt gcatcgccgc ctgtgagatc gtcggcgggg accgtccgc cgccgtgccc   480
gccgcctgcg cggcggagat gatccacacg atgtcgctga tccacgacga cctgccgtgt   540
atggacaacg acgacctccg ccgcggcaag ccgaccagtc acaagatgtt cggcgagaac   600
gttgctgtcc ttgcaggtga ttctttatta gcttttgcat tcgaattcat agcgacgggg    660
actaaggacg tggcgccgga gaggatcata gcatgtgtcg acgaattagc aaaggcggtc   720
gggggcgacg gtttagtggc ggggcaagtg gcagacataa aactcaccgg taataacgcg    780
gacgtgggac tagacatgtt agaattcata catatccaca agacccggat gctactggga    840
gcgtcggtgg taatggggc aattcttggg ggcggaagcc cccagcaagt ggataagcta   900
cggatctttg cgcaaaagat cgggttgctt tttcaagtgg tggacgacat actagatgtg    960
acgatgtcgt ccgaagaatt gggaaaaacg gcggggaagg acttggccac tgacaagacg   1020
acgtatccga agctttttggg agtcgagggg gcccagaat ttgcgaataa gttgtgcgag   1080
gaggcgaagg aacagctggc ggagttcgat tcggacaagg cggcgccgct ggcggcgctg   1140
gcggagtaca ttggtcggag gcagaattga                                     1170

SEQ ID NO: 9             moltype = DNA   length = 2499
FEATURE                  Location/Qualifiers
source                   1..2499
                         mol_type = other DNA
                         organism = synthetic construct
SEQUENCE: 9
atgcctttgt tttccctcct cggatcatcc ccctccccgc cgccccagct ctatattccg    60
gcagcatctc cttttcctcg cacctccgtt gttgcaggac tattttctgt ttggagaaat   120
```

```
acaacaaaca ctggctatcc ccttctgcaa tgtggtgcag tttccagagc tcctgctgaa    180
ggagaatata tagatgtgat tctgagtggt ttccctgtca gaaagtggcc atcgaatatt    240
gctacagagg gtgacacaca aaaggataag tataaaggcg aggaagtgag atcaaatgag    300
aggagggatc ggatggttga gatgatcaag tcaatgctga gatcaatgga cgatggagag    360
ataagcatat ctccttatga cactgcgtgg gtggcgttac tggaggatat tggaggcaaa    420
ggacagcctc agtttcccac cagcatcgaa tggatttcaa acaaccaact ggaggacggt    480
tcgtggggcg acagtgctgc ctattcagct cacgacagga tactcaacac attggcttgt    540
gttgtcgcat tgagatcctg gaaaatgcac caggacaaaa ctgataaagg ggttacattt    600
atcagaaaga acattcacag gctagacgaa gaaaaagaag agcacatgcc cataggtttc    660
gaagtggcac tgccatccct tattgaaaca gccaaaaagt tagggataga tgtgcccaat    720
gattccccag ccttgcaaaa aatttacgct agaagagaat taaagcttac aaggatacca    780
agggacatta tgcacaaggt gcccacaaca ttactgcaca gcttagaggg aatgtcatca    840
gggcttgagt ggcaagagct gttgaaatta cagtgtcctg acggctcatt tctcttttct    900
ccatcctcca ctgcctttgc attacaacaa actaaggatg agaattgtct caaatattta    960
ctcaagcatg ttagaaagtt caatggggga gttcctaatg tgtatccggt ggacttattt   1020
gagcgcctat gggctgtgga tcggctacaa aggctgggga tatcaaggta ttttcaacct   1080
gagattgaag agtgccttgg ttatgtacac agatactgga cagacaaggg gatttgttgg   1140
gcaagaaatt ctcaagttca ggccgttgat gacactgcca tgggattcag gcttctgagg   1200
ttgcatggct accgggtttc ggcagatgtt ttcaagaact ttaaacagga cgaagagttc   1260
ttctgcttcg cggggcagtc aaatcaggca gtgactggaa tgtataactt gtacagggct   1320
tctcaggtga tgtttccagg ggaagttata cttgcagaag cccgcaagtt ctcccacaag   1380
ttcttgcaag agaaaagggc taacaatgaa ctacttgata aatggattat aaccaaagac   1440
cttccaggag aggtgggatt tgcactggat attccatggt atgccagttt acctagaatt   1500
gagacaagat ttttcttgga acaatatggt ggtggtgatg atgtttggat tgggaagacc   1560
ttgtacaaga tgccctacat tgacaacagg gcctaccttg atctggcaaa gttagattac   1620
aataattgcc aggcattgca tcagatgag tggaaaagct ttcaaaaatg gtacagaagt   1680
tgcagacttg aggagtttgg gttgtcggag acgacccttg ttcaaactta ttacatcgca   1740
gcagcaagca tatttgagcc agaaagattg tatgagcggc ttgcatgggc taaaaactgcg   1800
attctaatgg agactgtcat gcggcattcg gaccaaaaga aactctccaa gcaacaaaag   1860
cacgcattag tcaatgaatt caaacattgt gcactgcttg gagaaaggta caaaacacga   1920
aacaacctga tagggaccct ggtcagaagt gtgaatgaac tctcattgga cgcaccattg   1980
gcgcgatacg cagacatcca atcacacttg catcgggcgt ggcaaaagtg gctaagctca   2040
tgggaggaag gggacacggg tgaaggcgat gcagagctgc tagtgtgcac tctaaatctg   2100
tgtggtggag gccgcagcag tcacagtcga tggtccgaca aattattgtt gtcgtatcct   2160
ccgtatcagc cccttgtgca gatcgccagc agagtctgtc accatctccg cctgtctcca   2220
acccgaaagg aggaggcaag gatgtgcgag cagaagctgc aaagtggcgt gagtggtggt   2280
gacatagaag ggagcatgca agagctggtg agattagcgc tggccaagag ccacagcgaa   2340
ttggagtttc gtgtgaagca aaacttcctc cttgtagcca ggagttatta ctacaccgca   2400
tattgtaacc ctgctactat caatctccac atagccaaag tcctctttga gactgtcgta   2460
ctagaatgct gtgatgacca tacccgccgt tacttctga                          2499
```

SEQ ID NO: 10          moltype = DNA   length = 725
FEATURE                Location/Qualifiers
source                 1..725
                       mol_type = other DNA
                       organism = synthetic construct
SEQUENCE: 10

```
tttgccagct tactatcctt cttgaaaata tgcactctat atcttttagt tcttaattgc    60
aacacataga tttgctgtat aacgaatttt atgctatttt ttaaatttgg agttcagtga   120
taaaagtgtc acagcgaatt tcctcacatg tagggaccga attgtttaca agttctctgt   180
accaccatgg agacatcaaa aattgaaaat ctatggaaag atatggacgg tagcaacaag   240
aatatagcac gagccgcgga gttcatttcg ttacttttga tatcactcac aactattgcg   300
aagcgcttca gtgaaaaaat cataaggaaa agttgtaaat attattggta gtattcgttt   360
ggtaaagtag aggggtaat ttttcccctt tattttgttc atacattctt aaattgcttt    420
gcctctcctt ttggaaagct atacttcgga gcactgttga gcgaaggctc attagatata   480
ttttctgtca ttttccttaa cccaaaaata agggaaaggg tccaaaaagc gctcggacaa   540
ctgttgaccg tgatccgaag gactggctat acagtgttca caaatagcc aagctgaaaa   600
taatgtgtag ctatgttcag ttagtttggc tagcaaagat ataaaagcag gtcggaaata   660
tttatgggca ttattatgca gagcatcaac atgataaaaa aaacagttg aatattccct    720
caaaa                                                               725
```

SEQ ID NO: 11          moltype = DNA   length = 700
FEATURE                Location/Qualifiers
source                 1..700
                       mol_type = other DNA
                       organism = synthetic construct
SEQUENCE: 11

```
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaaaaaac ccagacacgc   240
tcgacttcct gtcttcctat tgattgcagc ttccaatttc gtcacacaac aaggtcctag   300
cgacggctca caggttttgt aacaagcaat cgaaggttct ggaatggcgg gaaagggttt   360
agtaccacat gctatgatgc ccactgtgat ctccagagca aagttcgttc gatcgtactg   420
ttactctctc tctttcaaac agaattgtcc gaatcgtgtg acaacaacag cctgttctca   480
cacactcttt tcttctaacc aagggggtgg tttagtttag tagaacctcg tgaaacttac   540
atttacatat atataaactt gcataaattg gtcaatgcaa gaaatacata tttggtcttt   600
tctaattcgt agttttcaa gttcttagat gctttctttt tctcttttttt acagatcatc    660
aaggaagtaa ttatctactt tttacaacaa atataaaaca                          700
```

```
SEQ ID NO: 12          moltype = DNA   length = 401
FEATURE                Location/Qualifiers
source                 1..401
                       mol_type = other DNA
                       organism = synthetic construct
SEQUENCE: 12
aaacttagat tagattgcta tgctttcttt ctaatgagca agaagtaaaa aaagttgtaa    60
tagaacaaga aaaatgaaac tgaaacttga gaaattgaag accgtttatt aacttaaata   120
tcaatgggag gtcatcgaaa gagaaaaaaa tcaaaaaaaa aattttcaag aaaaagaaac   180
gtgataaaaa ttttttattgc cttttttcgac gaagaaaaag aaacgaggcg gtctcttttt   240
tcttttccaa acctttagta cgggtaatta acgacaccct agaggaagaa agaggggaaa   300
tttagtatgc tgtgcttggg tgttttgaag tggtacggcg atgcgcggag tccgagaaaa   360
tctggaagag taaaaaagga gtagaaacat tttgaagcta t                      401

SEQ ID NO: 13          moltype = DNA   length = 39
FEATURE                Location/Qualifiers
source                 1..39
                       mol_type = other DNA
                       organism = synthetic construct
SEQUENCE: 13
ctgcccagcc ggcgatggcc accaagaact tgcccccgt                          39

SEQ ID NO: 14          moltype = DNA   length = 49
FEATURE                Location/Qualifiers
source                 1..49
                       mol_type = other DNA
                       organism = synthetic construct
SEQUENCE: 14
cagtggtggt ggtggtggtg aacgaacaca ccctcagtat agaactttg              49

SEQ ID NO: 15          moltype = DNA   length = 39
FEATURE                Location/Qualifiers
source                 1..39
                       mol_type = other DNA
                       organism = synthetic construct
SEQUENCE: 15
taagaaggag atataccatg aaacgtcccc ggagttccg                          39

SEQ ID NO: 16          moltype = DNA   length = 50
FEATURE                Location/Qualifiers
source                 1..50
                       mol_type = other DNA
                       organism = synthetic construct
SEQUENCE: 16
cagtggtggt ggtggtggtg ctttacaggc aaagggtttt tcaatttggg            50

SEQ ID NO: 17          moltype = DNA   length = 37
FEATURE                Location/Qualifiers
source                 1..37
                       mol_type = other DNA
                       organism = synthetic construct
SEQUENCE: 17
caccagctga gctcattgcc tcaccacgac ctccggc                            37

SEQ ID NO: 18          moltype = DNA   length = 49
FEATURE                Location/Qualifiers
source                 1..49
                       mol_type = other DNA
                       organism = synthetic construct
SEQUENCE: 18
cagtggtggt ggtggtggtg aacgaacaca ccctcagtat agaactttg              49

SEQ ID NO: 19          moltype = DNA   length = 44
FEATURE                Location/Qualifiers
source                 1..44
                       mol_type = other DNA
                       organism = synthetic construct
SEQUENCE: 19
gtcagctccc gaccaccgca tcatatttta gccgacttgg cgtc                    44

SEQ ID NO: 20          moltype = DNA   length = 50
FEATURE                Location/Qualifiers
source                 1..50
                       mol_type = other DNA
                       organism = synthetic construct
SEQUENCE: 20
cagtggtggt ggtggtggtg ctttacaggc aaagggtttt tcaatttggg            50
```

-continued

```
SEQ ID NO: 21              moltype = DNA   length = 58
FEATURE                    Location/Qualifiers
source                     1..58
                           mol_type = other DNA
                           organism = synthetic construct
SEQUENCE: 21
gaatttgaca atgttaagct ttgttaaaca gcttggcgta atcatggtca tagctgtt      58

SEQ ID NO: 22              moltype = DNA   length = 42
FEATURE                    Location/Qualifiers
source                     1..42
                           mol_type = other DNA
                           organism = synthetic construct
SEQUENCE: 22
ggtagttcca cgcggccgat ccgagttcta attcactggc cg                       42

SEQ ID NO: 23              moltype = DNA   length = 40
FEATURE                    Location/Qualifiers
source                     1..40
                           mol_type = other DNA
                           organism = synthetic construct
SEQUENCE: 23
ggccagtgaa ttagaactcg gatcggccgc gtggaactac                          40

SEQ ID NO: 24              moltype = DNA   length = 48
FEATURE                    Location/Qualifiers
source                     1..48
                           mol_type = other DNA
                           organism = synthetic construct
SEQUENCE: 24
aaggatagta agctggcaaa tgttgattgt ctaactgcgt tcttttgt                 48

SEQ ID NO: 25              moltype = DNA   length = 56
FEATURE                    Location/Qualifiers
source                     1..56
                           mol_type = other DNA
                           organism = synthetic construct
SEQUENCE: 25
aagaacgcag ttagacaatc aacatttgcc agcttactat ccttcttgaa aatatg        56

SEQ ID NO: 26              moltype = DNA   length = 59
FEATURE                    Location/Qualifiers
source                     1..59
                           mol_type = other DNA
                           organism = synthetic construct
SEQUENCE: 26
aattttggag aaacgtcggt tttgagggaa tattcaactg ttttttttta tcatgttga     59

SEQ ID NO: 27              moltype = DNA   length = 54
FEATURE                    Location/Qualifiers
source                     1..54
                           mol_type = other DNA
                           organism = synthetic construct
SEQUENCE: 27
agttgaatat tccctcaaaa ccgacgtttc tccaaaattc atttcaattt tttc          54

SEQ ID NO: 28              moltype = DNA   length = 45
FEATURE                    Location/Qualifiers
source                     1..45
                           mol_type = other DNA
                           organism = synthetic construct
SEQUENCE: 28
tagaaacatt ttgaagctat tcaattctgc ctccgaccaa tgtac                    45

SEQ ID NO: 29              moltype = DNA   length = 58
FEATURE                    Location/Qualifiers
source                     1..58
                           mol_type = other DNA
                           organism = synthetic construct
SEQUENCE: 29
attggtcgga ggcagaattg aatagcttca aaatgtttct actccttttt tactcttc      58

SEQ ID NO: 30              moltype = DNA   length = 56
FEATURE                    Location/Qualifiers
source                     1..56
                           mol_type = other DNA
                           organism = synthetic construct
SEQUENCE: 30
aggagggaaa acaaaggcat cttagattag attgctatgc tttctttcta atgagc        56
```

-continued

```
SEQ ID NO: 31            moltype = DNA   length = 42
FEATURE                  Location/Qualifiers
source                   1..42
                         mol_type = other DNA
                         organism = synthetic construct
SEQUENCE: 31
gcatagcaat ctaatctaag atgcctttgt tttccctcct cg                        42

SEQ ID NO: 32            moltype = DNA   length = 46
FEATURE                  Location/Qualifiers
source                   1..46
                         mol_type = other DNA
                         organism = synthetic construct
SEQUENCE: 32
gcataaattt ttagttaaag ggtcagaagt aacggcgggt atggtc                    46

SEQ ID NO: 33            moltype = DNA   length = 53
FEATURE                  Location/Qualifiers
source                   1..53
                         mol_type = other DNA
                         organism = synthetic construct
SEQUENCE: 33
catacccgcc gttacttctg accctttaac taaaaattta tgcatttggc tcc            53

SEQ ID NO: 34            moltype = DNA   length = 58
FEATURE                  Location/Qualifiers
source                   1..58
                         mol_type = other DNA
                         organism = synthetic construct
SEQUENCE: 34
tatgaccatg attacgccaa gctgtttaac aaagcttaac attgtcaaat tcttcagg       58

SEQ ID NO: 35            moltype = DNA   length = 58
FEATURE                  Location/Qualifiers
source                   1..58
                         mol_type = other DNA
                         organism = synthetic construct
SEQUENCE: 35
tgttaatact tctaactata gttttagagc tagaaatagc aagttaaaat aaggctag       58

SEQ ID NO: 36            moltype = DNA   length = 51
FEATURE                  Location/Qualifiers
source                   1..51
                         mol_type = other DNA
                         organism = synthetic construct
SEQUENCE: 36
tatagttaga agtattaaca gatcatttat ctttcactgc ggagaagttt c              51

SEQ ID NO: 37            moltype = DNA   length = 39
FEATURE                  Location/Qualifiers
source                   1..39
                         mol_type = other DNA
                         organism = synthetic construct
SEQUENCE: 37
gtaaggggg sggggsgggg satggattcg cggctggag                            39

SEQ ID NO: 38            moltype = DNA   length = 44
FEATURE                  Location/Qualifiers
source                   1..44
                         mol_type = other DNA
                         organism = synthetic construct
SEQUENCE: 38
gaatgtaagc gtgacataac tcaccaaaca tccctcaggt atcg                      44

SEQ ID NO: 39            moltype = DNA   length = 47
FEATURE                  Location/Qualifiers
source                   1..47
                         mol_type = other DNA
                         organism = synthetic construct
SEQUENCE: 39
accaaacctc tggcgaagaa tttgccagct tactatcctt cttgaaa                   47

SEQ ID NO: 40            moltype = DNA   length = 59
FEATURE                  Location/Qualifiers
source                   1..59
                         mol_type = other DNA
                         organism = synthetic construct
SEQUENCE: 40
```

```
ggggggcaagt tcttggtcat ttttgaggga atattcaact gttttttttt atcatgttg    59

SEQ ID NO: 41            moltype = DNA   length = 40
FEATURE                  Location/Qualifiers
source                   1..40
                         mol_type = other DNA
                         organism = synthetic construct
SEQUENCE: 41
agttgaatat tccctcaaaa atgaccaaga acttgccccc                            40

SEQ ID NO: 42            moltype = DNA   length = 49
FEATURE                  Location/Qualifiers
source                   1..49
                         mol_type = other DNA
                         organism = synthetic construct
SEQUENCE: 42
cattttgaag ctatgagctc aacgaacaca ccctcagtat agaactttg                 49

SEQ ID NO: 43            moltype = DNA   length = 61
FEATURE                  Location/Qualifiers
source                   1..61
                         mol_type = other DNA
                         organism = synthetic construct
SEQUENCE: 43
caaagttcta tactgagggt gtgttcgttg agctcatagc ttcaaaatgt ttctactcct    60
t                                                                     61

SEQ ID NO: 44            moltype = DNA   length = 59
FEATURE                  Location/Qualifiers
source                   1..59
                         mol_type = other DNA
                         organism = synthetic construct
SEQUENCE: 44
gaactccggg gacgtttcat actagttcta gaaaacttag attagattgc tatgctttc     59

SEQ ID NO: 45            moltype = DNA   length = 41
FEATURE                  Location/Qualifiers
source                   1..41
                         mol_type = other DNA
                         organism = synthetic construct
SEQUENCE: 45
ctaagttttc tagaactagt atgaaacgtc cccggagttc c                         41

SEQ ID NO: 46            moltype = DNA   length = 50
FEATURE                  Location/Qualifiers
source                   1..50
                         mol_type = other DNA
                         organism = synthetic construct
SEQUENCE: 46
atccatsccc cscccccsccc cctttacagg caaagggttt ttcaatttgg               50

SEQ ID NO: 47            moltype = DNA   length = 45
FEATURE                  Location/Qualifiers
source                   1..45
                         mol_type = other DNA
                         organism = synthetic construct
SEQUENCE: 47
acctgaggga tgtttggtga gttatgtcac gcttacattc acgcc                     45

SEQ ID NO: 48            moltype = DNA   length = 41
FEATURE                  Location/Qualifiers
source                   1..41
                         mol_type = other DNA
                         organism = synthetic construct
SEQUENCE: 48
aaggatagta agctggcaaa ttcttcgcca gaggtttggt c                         41

SEQ ID NO: 49            moltype = DNA   length = 10251
FEATURE                  Location/Qualifiers
source                   1..10251
                         mol_type = other DNA
                         organism = synthetic construct
SEQUENCE: 49
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accataccac agcttttcaa ttcaattcat catttttttt ttattctttt ttttgatttc    240
ggtttctttg aaatttttt gattcggtaa tctccgaaca gaaggaagaa cgaaggaagg    300
agcacagact tagattggta tatatacgca tatgtagtgt tgaagaaaca tgaaattgcc    360
```

-continued

```
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa ttttttactc ttcgaagaca gaaaatttgc tgacattggt aatacagtca   720
aattgcagta ctctgcgggt gtatacgaaa tagcagaatg ggcagacatt acgaatgcac   780
acggtgtggt gggcccaggt attgttagcg gtttgaagca ggcggcagaa gaagtaacaa   840
aggaacctag aggccttttg atgttagcag aattgtcatg caagggctcc ctatctactg   900
gagaatatac taagggtact gttgacattg cgaagagcga caaagatttt gttatcggct   960
ttattgctca aagagacatg ggtggaagag atgaaggtta cgattggttg attatgacac  1020
ccggtgtggg tttagatgac aagggagacg cattgggtca acagtataga accgtggatg  1080
atgtggtctc tacaggatct gacattatta ttgttggaag aggactattt gcaaagggaa  1140
gggatgctaa ggtagagggt gaacgttaca gaaaagcagg ctgggaagca tatttgagaa  1200
gatgcggcca gcaaaactaa aaaactgtat tataagtaaa tgcatgtata ctaaactcac  1260
aaattagagc ttcaatttaa ttatatcagt tattacccta tgcggtgtga aataccgcac  1320
agatgcgtaa ggagaaaata ccgcatcagg catagcttca aaatgtttct actccttttt  1380
tactcttcca gattttctcg gactccgcgc atcgccgtac cacttcaaaa cacccaagca  1440
cagcatacta aatttcccct cttcttcct ctagggtgtc gttaattacc cgtactaaag   1500
gtttggaaaa gaaaaaagag accgcctcgt ttcttttttct tcgtcgaaaa aggcaataaa  1560
aatttttatc acgtttcttt ttcttgaaaa ttttttttt gatttttttc tctttcgatg   1620
acctcccatt gatatttaag ttaataaacg gtcttcaatt tctcaagttt cagtttcatt  1680
tttcttgttc tattacaact tttttactt cttgctcatt agaaagaaag catagcaatc   1740
taatctaagt tttctagaac tagtggatcc cccgggaaaa atggacaaga agtactccat  1800
tgggctcgat atcggcacaa acagcgtcgg ttgggccgtc attacggacg agtacaaggt  1860
gccgagcaaa aaattcaaag ttctgggcaa taccgatcgc cacagcataa agaagaacct  1920
cattggcgcc ctcctgttcg actccgggga gacggccgaa gccacgcggc tcaaaagaac  1980
agcacggcgc agatataccc gcagaaagaa tcggatctgc tacctgcagg agatctttag  2040
taatgagatg gctaaggtgg atgactcttt cttccatagg ctggaggagt cctttttggt  2100
ggaggaggat aaaaagcacg agcgccaccc aatctttggc aatatcgtgg acgaggtggc  2160
gtaccatgaa aagtacccaa ccatatatca tctgaggaag aagcttgtag acagtactga  2220
taaggctgac ttgcggttga tctatctcgc gctggcgcat atgatcaaat ttcgggggaca  2280
cttcctcatc gaggggggacc tgaacccaga caacagcgat gtcgacaaac tctttatcca  2340
actggttcag acttacaatc agcttttcga agagaacccg atcaacgcat ccggagttga  2400
cgccaaagca atcctgagcg ctaggctgtc caaatcccgg cggctcgaaa acctcatcgc  2460
acagctccct ggggagaaga agaacggcct gtttggtaat cttatcgccc tgtcactcgg  2520
gctgacccc aactttaaat ctaacttcga cctggccgaa gatgccaagc ttcaactgag   2580
caaagacacc tacgatgatg atctcgacaa tctgctggcc cagatcggcg accagtacgc  2640
agacctttt ttggcggcaa agaacctgtc agacgccatt ctgctgagtg atattctgcg   2700
agtgaacacg gagatcacca aagctccgct gagcgctagt atgatcaagc gctatgatga  2760
gcaccaccaa gacttgactt tgctgaaggc ccttgtcaga cagcaactgc ctgagaagta  2820
caaggaaatt ttcttcgatc agtctaaaaa tggctacgcc ggatacattg acggcggagc  2880
aagccaggag gaattttaca aatttattaa gcccatcttg gaaaaaatgc acggcaccga  2940
ggagctgctg gtaaagctta acagagaaga tctgttgcgc aaacagcgca ctttcgacaa  3000
tggaagcatc ccccaccaga ttcacctggg cgaactgcac gctatcctca ggcggcaaga  3060
ggatttctac cccttttttga aagataacag ggaaaagatt gagaaaatcc tcacatttcg  3120
gataccctac tatgtaggcc ccctcgcccg gggaaattgc agattcgcgt ggatgactcg  3180
caaatcagaa gagaccatca ctccctggaa cttcgaggaa gtcgtggata aggggggcctc  3240
tgcccagtcc ttcatcgaaa ggatgactaa cttttgataaa aatctgccta acgaaaaggt  3300
gcttcctaaa cactctctgc tgtacgagta cttcacagtt tataacgagc tcaccaaggt  3360
caaatacgtc acagaaggga tgagaaagcc agcattcctg tctggagagc agaagaaagc  3420
tatcgtggac ctcctcttca agacgaaccg gaaagttacc gtgaaacagc tcaaagaaga  3480
ctatttcaaa aagattgaat gtttcgactc tgttgaaatc agcggagtgg aggatcgctt  3540
caacgcatcc ctgggaacgt atcacgatct cctgaaaatc attaaagaca aggacttcct  3600
ggacaatgag gagaacgagg acattcttga ggacattgct ctcacccta cgttgtttga   3660
agatagggag atgattgaag aacgcttgaa aacttacgct catctcttcg acgacaaagt  3720
catgaaacag ctcaagaggc gccgatatac aggatggggg cggctgtcaa gaaaactgat  3780
caatgggatc cgagacaagc agagtggaaa gacaatcctg gattttctta gtccgatgg   3840
atttgtcaac cggaacttca tgcagttgat ccatgatgac tctctcacct ttaaggagga  3900
catccagaaa gcacaagttt ctggccaggg ggacagtctt cacgagcaca tcgctaatct  3960
tgcaggtagc ccagctatca aaaagggaat actgcagacc gttaaggtcg tggatgaact  4020
cgtcaaagta atgggaaggc ataagcccga gaatatcgtt atcgagatgg cccgagaaa   4080
ccaaactacc cagaagggac agaagaacag tagggaaagg atgaagagga ttgaagaggg  4140
tataaaagaa ctggggtccc aaatccttaa ggaacaccga gttgaaaaca cccagctttc  4200
gaatgagaag ctctacctgt actacctgca gaacggcagg gacatgtacg tggatcagga  4260
actggacatc aatcggctct ccgactacga cgtggatcat atcgtgcccc agtcttttct  4320
caaagatgat tctattgata ataaagtgtt gacaagatcc gataaaaata gagggaagag  4380
tgataacgtc ccctcagaag aagttgtcaa gaaaatgaaa aattattggc ggcagctgct  4440
gaacgccaaa ctgatcacac aacggaagtt cgataatctg actaaggctg aacgaggtgg  4500
cctgtctgag ttggataaag ccggcttcat caaaaggcag cttgttgaga cacgccagat  4560
caccaagcac gtggcccaaa ttctcgattc acgcatgaac accaagtacg atgaaaatga  4620
caaactgatt cgagaggtga aagttattac tctgaagtct aagctggtct cagatttcag  4680
aaaggacttt cagttttata aggtgagaga gatcaacaat taccaccatg cgcatgatgc  4740
ctacctgaat gcagtggtag gcactgcact tatcaaaaaa tatccaaagc ttgaatctga  4800
atttgtttac ggagactata agtgtacga tgttaggaaa atgatcgcaa agtctgagca  4860
ggaaataggc aaggccaccg ctaagtactt cttttacagc aatattatga attttttcaa  4920
gaccgagatt acactggcca atggagagat tcggaagcga ccacttatcg aaacaaacgg  4980
agaaacagga gaaatcgtgt gggacaaggg tagggatttc gcgacagtcc ggaaggtcct  5040
gtccatgccg caggtgaaca tcgttaaaaa gaccgaagta cagaccggag gcttctccaa  5100
```

-continued

```
ggaaagtatc ctcccgaaaa ggaacagcga caagctgatc gcacgcaaaa aagattggga   5160
ccccaagaaa tacggcggat tcgattctcc tacagtcgct tacagtgtac tggttgtggc   5220
caaagtggag aaagggaagt ctaaaaaact caaaagcgtc aaggaactgc tgggcatcac   5280
aatcatggag cgatcaagct tcgaaaaaaa ccccatcgac tttctcgagg cgaaaggata   5340
taaagaggtc aaaaaagacc tcatcattaa gcttcccaag tactctctct ttgagcttga   5400
aaacggccgg aaacgaatgc tcgctagtgc gggcgagctg cagaaaggta acgagctggc   5460
actgccctct aaatacgtta atttcttgta tctggccagc cactatgaaa agctcaaagg   5520
gtctcccgaa gataatgagc agaagcagct gttcgtggaa caacacaaac actaccttga   5580
tgagatcatc gagcaaataa gcgaattctc caaaagagtg atcctcgccg acgctaacct   5640
cgataaggtg ctttctgctt acaataagca cagggataag cccatcaggg agcaggcaga   5700
aaacattatc cacttgttta ctctgaccaa cttgggcgcg cctgcagcct tcaagtactt   5760
cgacaccacc atagacagaa agcggtacac ctctacaaag gaggtcctgg acgccacact   5820
gattcatcag tcaattacgg ggctctatga aacaagaatc gacctctctc agctcggtgg   5880
agacagcagg gctgacccca agaagaagag gaaggtgtga tctcttctcg agtcatgtaa   5940
ttagttatgt cacgcttaca ttcacgcccc cccccacat ccgctctaac cgaaaaggaa    6000
ggagttagac aacctgaagt ctaggtccct atttatttt ttatagttat gttagtatta    6060
agaacgttat ttatatttca aatttttctt ttttttctgt acagacgcgt gtacgcatgt   6120
aacattatac tgaaaacctt gcttgagaag gttttgggac gctcgaaggc tttaatttgc   6180
ctcgaggtcg acggtatcga taagcttgat atcgaattcc tgcagcccgg gggatccact   6240
agttctttga aaagataatg tatgattatg ctttcactca tatttataca gaaacttgat   6300
gttttcttc gagtatatac aaggtgatta catgtacgtt tgaagtacaa ctctagattt    6360
tgtagtgccc tcttgggcta gcggtaaagg tgcgcatttt ttcacaccct acaatgttct   6420
gttcaaaaga ttttggtcaa acgctgtaga agtgaaagtt ggtgcgcatg tttcggcgtt   6480
cgaaacttct ccgcagtgaa agataaatga tcgcctttat ggagaaaaat gggttttaga   6540
gctagaaata gcaagttaaa ataaggctag tccgttatca acttgaaaaa gtggcaccga   6600
gtcggtggtg ctttttttgt tttttatgtc gagctccagc ttttgttccc tttagtgagg   6660
gttaattgcg cgcttggcgt aatcatggtc atagctgttt cctgtgtgaa attgttatcc   6720
gctcacaatt ccacacaaca taggagccgg aagcataaag tgtaaagcct ggggtgccta   6780
atgagtgagg taactcacat taattgcgtt gcgctcactg cccgctttcc agtcgggaaa   6840
cctgtcgtgc cagctgcatt aatgaatcgg ccaacgcgcg gggagaggcg gtttgcgtat   6900
tgggcgctct tccgcttcct cgctcactga ctcgctgcgc tcggtcgttc ggctgcggcg   6960
agcggtatca gctcactcaa aggcggtaat acggttatcc acagaatcag gggataacgc   7020
aggaaagaac atgtgagcaa aaggccagca aaaggccagg aaccgtaaaa aggccgcgtt   7080
gctggcgttt ttccataggc tccgcccccc tgacgagcat cacaaaaatc gacgctcaag   7140
tcagaggtgg cgaaacccga caggactata aagataccag gcgtttcccc ctggaagctc   7200
cctcgtgcgc tctcctgttc cgaccctgcc gcttaccgga tacctgtccg cctttctccc   7260
ttcgggaagc gtggcgcttt ctcatagctc acgctgtagg tatctcagtt cggtgtaggt   7320
cgttcgctcc aagctgggct gtgtgcacga accccccgtt cagcccgacc gctgcgcctt   7380
atccggtaac tatcgtcttg agtccaaccc ggtaagacac gacttatcgc cactggcagc   7440
agccactggt aacaggatta gcagagcgag gtatgtaggc ggtgctacag agttcttgaa   7500
gtggtggcct aactacggct acactagaag gacagtattt ggtatctgcg ctctgctgaa   7560
gccagttacc ttcggaaaaa gagttggtag ctcttgatcc ggcaaacaaa ccaccgctgg   7620
tagcggtggt ttttttgttt gcaagcagca gattacgcgc agaaaaaaag gatctcaaga   7680
agatcctttg atcttttcta cggggtctga cgctcagtgg aacgaaaact cacgttaagg   7740
gattttggtc atgagattat caaaaaggat cttcacctag atccttttaa attaaaaatg   7800
aagttttaaa tcaatctaaa gtatatatga gtaaacttgg tctgacagtt accaatgctt   7860
aatcagtgag gcacctatct cagcgatctg tctatttcgt tcatccatag ttgcctgact   7920
ccccgtcgtg tagataacta cgatacggga gggcttacca tctggcccca gtgctgcaat   7980
gataccgcga gacccacgct caccggctcc agatttatca gcaataaacc agccagccgg   8040
aagggccgag cgcagaagtg gtcctgcaac tttatccgcc tccatccagt ctattaattg   8100
ttgccgggaa gctagagtaa gtagttcgcc agttaatagt ttgcgcaacg ttgttgccat   8160
tgctacaggc atcgtggtgt cacgctcgtc gtttggtatg gcttcattca gctccggttc   8220
ccaacgatca aggcgagtta catgatcccc catgttgtgc aaaaaagcgg ttagctcctt   8280
cggtcctccg atcgttgtca gaagtaagtt ggccgcagtg ttatcactca tggttatggc   8340
agcactgcat aattctctta ctgtcatgcc atccgtaaga tgcttttctg tgactggtga   8400
gtactcaacc aagtcattct gagaatagtg tatgcggcga ccgagttgct cttgcccggc   8460
gtcaatacgg gataataccg cgccacatag cagaacttta aaagtgctca tcattggaaa   8520
acgttcttcg gggcgaaaac tctcaaggat cttaccgctg ttgagatcca gttcgatgta   8580
acccactcgt gcacccaact gatcttcagc atcttttact ttcaccagcg tttctgggtg   8640
agcaaaaaca ggaaggcaaa atgccgcaaa aaagggaata agggcgacac ggaaatgttg   8700
aatactcata ctcttccttt ttcaatatta ttgaagcatt tatcagggtt attgtctcat   8760
gagcggatac atatttgaat gtatttagaa aaataaacaa ataggggttc cgcgcacatt   8820
tccccgaaaa gtgccacctg aacgaagcat ctgtgcttca ttttgtagaa caaaaatgca   8880
acgcgagagc gctaattttt caaacaaaga atctgagctg catttttaca gaacagaaat   8940
gcaacgcgaa agcgctattt taccaacgaa gaatctgtgc ttcatttttg taaacaaaa   9000
atgcaacgcg agagcgctaa ttttttcaaac aaagaatctg agctgcattt ttacagaaca   9060
gaaatgcaac gcgagagcgc tatttttacca acaaagaatc tatacttctt ttttgttcta   9120
caaaaatgca tcccgagagc gctatttttc taacaaagca tcttagatta cttttttttct   9180
cctttgtgcg ctctataatg cagtctcttg ataacttttt gcactgtagg tccgttaagg   9240
ttagaagaag gctactttgg tgtctatttt ctcttccata aaaaaagcct gactccactt   9300
cccgcgttta ctgattacta gcgaagctgc gggtgcattt tttcaagata aaggcatccc   9360
cgattatatt ctataccgat gtggattgcg catactttgt gaacagaaag tgatagcgtt   9420
gatgattctt cattggtcag aaaattatga acggtttctt ctattttgtc tctatatact   9480
acgtatagga aatgtttaca ttttcgtatt gttttcgatt cactctatga atagttcttac   9540
ctacaatttt tttgtctaaa gagtaatact agagataaac ataaaaaatg tagaggtcga   9600
gtttagatgc aagttcaagg agcgaaaggt ggatgggtag ttatataagg atatagcac   9660
agagatatat agcaaagaga tacttttgag caatgtttgt ggaagcggta ttcgcaatat   9720
tttagtagct cgttacagtc cggtgcgttt ttggtttttt gaaagtgcgt cttcagagcg   9780
cttttggttt tcaaaagcgc tctgaagttc ctatactttc tagagaatag gaacttcgga   9840
```

-continued

```
ataggaactt caaagcgttt ccgaaaacga gcgcttccga aaatgcaacg cgagctgcgc  9900
acatacagct cactgttcac gtcgcaccta tatctgcgtg ttgcctgtat atatatatac  9960
atgagaagaa cggcatagtg cgtgtttatg cttaaatgcg tacttatatg cgtctattta  10020
tgtaggatga aaggtagtct agtacctcct gtgatattat cccattccat gcggggtatc  10080
gtatgcttcc ttcagcacta ccctttagct gttctatatg ctgccactcc tcaattggat  10140
tagtctcatc cttcaatgct atcatttcct ttgatattgt atcatactaa gaaaccatta  10200
ttatcatgac attaacctat aaaaataggc gtatcacgag gccctttcgt c           10251
```